US011504487B2

(12) United States Patent
O'Dea

(10) Patent No.: US 11,504,487 B2
(45) Date of Patent: Nov. 22, 2022

(54) METHOD AND APPARATUS FOR INSUFFLATING A CAVITY IN THE BODY OF A HUMAN OR ANIMAL SUBJECT

(71) Applicant: PALLIARE LIMITED, Galway (IE)

(72) Inventor: John O'Dea, Galway (IE)

(73) Assignee: PALLIARE LIMITED, Galway (IE)

( * ) Notice: Subject to any disclaimer, the term of this patent is extended or adjusted under 35 U.S.C. 154(b) by 307 days.

(21) Appl. No.: 16/070,164

(22) PCT Filed: Jan. 16, 2017

(86) PCT No.: PCT/IE2017/000001
§ 371 (c)(1),
(2) Date: Jul. 13, 2018

(87) PCT Pub. No.: WO2017/122188
PCT Pub. Date: Jul. 20, 2017

(65) Prior Publication Data
US 2019/0060585 A1    Feb. 28, 2019

(30) Foreign Application Priority Data

Jan. 15, 2016  (IE) .................................. S2016/0017
May 5, 2016   (IE) .................................. S2016/0121

(51) Int. Cl.
*A61M 13/00*    (2006.01)
*A61M 39/22*    (2006.01)
(Continued)

(52) U.S. Cl.
CPC ............. *A61M 13/003* (2013.01); *A61D 7/00* (2013.01); *A61M 13/00* (2013.01);
(Continued)

(58) Field of Classification Search
CPC .............. A61M 13/003; A61M 39/227; A61M 2039/226; A61M 2039/242;
(Continued)

(56) References Cited

U.S. PATENT DOCUMENTS 5,476,447 A * 12/1995 Noda ................. A61B 18/1482
604/26
2011/0306972 A1 * 12/2011 Widenhouse ...... A61B 18/1442
606/45
(Continued)

FOREIGN PATENT DOCUMENTS

DE        42 19 859 B4    12/2005
DE    10 2012 009078 A1   11/2013
(Continued)

OTHER PUBLICATIONS

International Search Report for PCT/IE2017/000001 dated Jun. 6, 2017.

*Primary Examiner* — Lauren P Farrar
*Assistant Examiner* — Hamza A Darb
(74) *Attorney, Agent, or Firm* — Sughrue Mion, PLLC

(57) ABSTRACT

An insufflator for insufflating a body cavity includes a compressed air vessel and a flow control valve for delivering insufflating air to the cavity through a first trocar. A discharge control valve at an outlet port of a second trocar exhausts insufflating air from the cavity. A pressure sensor on the first trocar monitors cavity pressure, and a microcontroller operates the flow control valve for maintaining a predefined working pressure in the cavity. A foot operated switch is operable by a surgeon for opening and closing the discharge control valve. When the pressure in the cavity drops below the predefined working pressure, the flow control valve increases the insufflating air to the cavity, thereby increasing the insufflating air flow through the cavity for removing undesirable gases. The apparatus and
(Continued)

Figure 1:
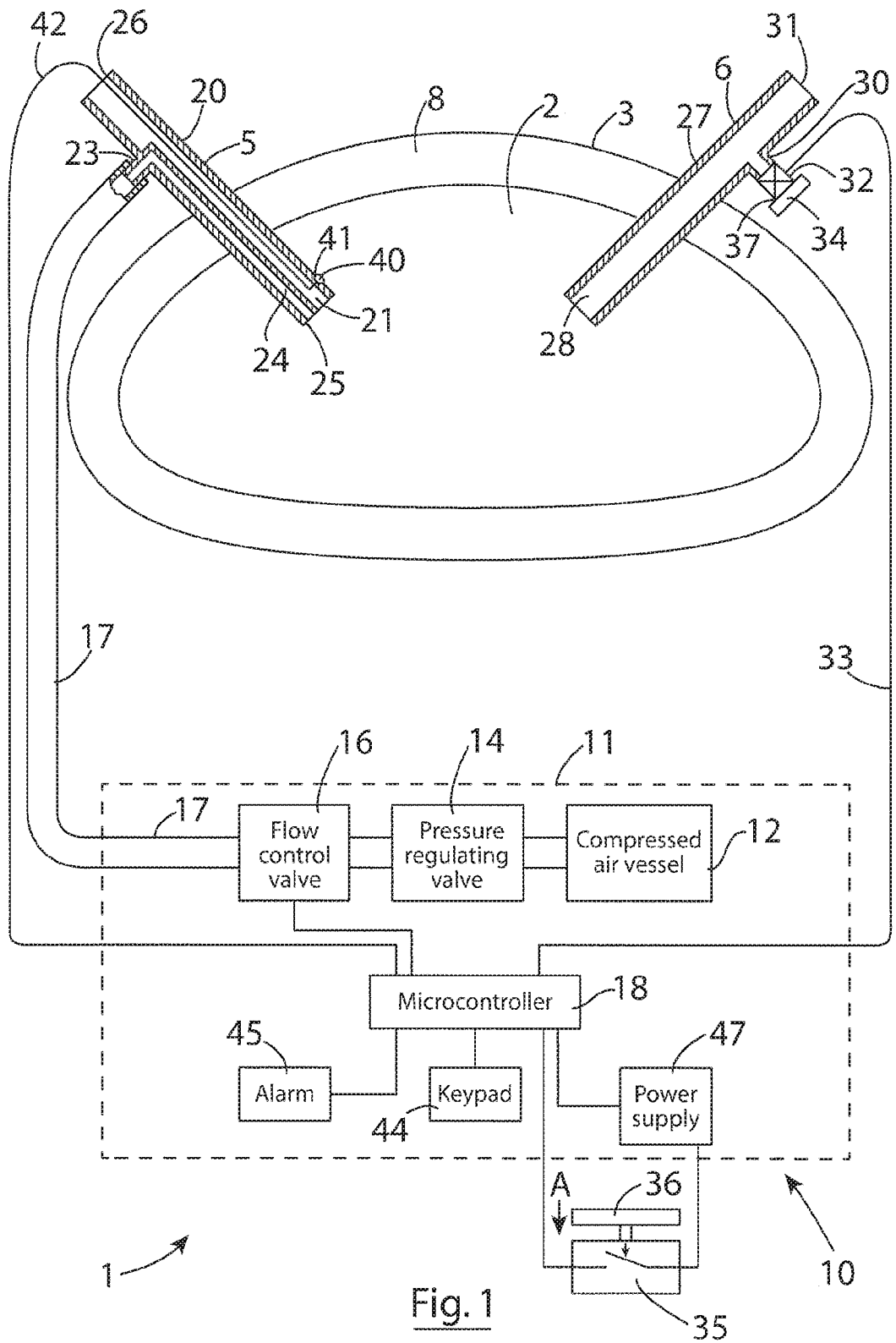

insufflator may also be adapted for removing smoke, nitrogen or other undesirable gases during both cauterisation and cryogenic procedures.

20 Claims, 7 Drawing Sheets

(51) Int. Cl.
 A61M 39/24 (2006.01)
 A61D 7/00 (2006.01)
 A61B 17/34 (2006.01)
(52) U.S. Cl.
 CPC ....... *A61M 39/227* (2013.01); *A61B 17/3474* (2013.01); *A61M 2039/226* (2013.01); *A61M 2039/242* (2013.01); *A61M 2202/0225* (2013.01); *A61M 2205/18* (2013.01); *A61M 2205/3334* (2013.01); *A61M 2205/3344* (2013.01); *A61M 2205/75* (2013.01)

(58) Field of Classification Search
 CPC ...... A61M 2202/0225; A61M 2205/18; A61M 2205/3334; A61M 2205/3344; A61M 2205/75; A61M 13/00; A61B 17/3474; A61D 7/00
 See application file for complete search history.

(56) References Cited

U.S. PATENT DOCUMENTS

2013/0211320 A1* 8/2013 Alkhamesi ........... A61M 11/007
 604/24
2018/0280634 A1* 10/2018 O'Dea ................ A61M 13/003

FOREIGN PATENT DOCUMENTS

DE 10 2012 110889 A1 5/2014
WO 2016/071893 A1 5/2016

* cited by examiner

METHOD AND APPARATUS FOR INSUFFLATING A CAVITY IN THE BODY OF A HUMAN OR ANIMAL SUBJECT

CROSS REFERENCE TO RELATED APPLICATIONS

This application is a National Stage of International Application No. PCT/IE2017/000001 filed Jan. 16, 2017, claiming priority based on Irish Patent Application Nos. S2016/0017 filed Jan. 15, 2016 and S2016/0121 filed May 5, 2016.

The present invention relates to a method and apparatus for insufflating a cavity in the body of a human or animal subject, and the invention also relates to a method for insufflating a cavity in the body of a human or animal subject. The invention also relates to a method and apparatus for removing an undesirable gas from a cavity in the body of a human or animal subject during, for example, a laparoscopic procedure and the invention also relates to a method and apparatus for avoiding over pressurisation of a cavity in the body of a human or animal subject during insufflating thereof.

During laparoscopic procedures, for example, procedures carried out in the peritoneal cavity, the stomach, and other cavities in a human or animal subject, such as procedures for removing cancerous tissue, a gall bladder, and other such procedures, in general organs or parts thereof and tissues are cut away using cauterising instruments, which thus result in the generation of smoke due to the cauterising process. The presence of such smoke in the peritoneal cavity or other such cavity, in which a procedure is being carried out by laparoscopic surgery, is undesirable in that it results in poor visibility in the relevant cavity, thereby impeding the carrying out of the procedure. Accordingly, it is desirable that the smoke and any other undesirable gases resulting from cauterising and other such procedures should be removed as quickly as possible from the cavity in which the procedure is being carried out.

In carrying out a cryogenic procedure in a cavity, for example, the stomach, oesophagus, a lung or other vessel, lumen or organ in the body of a human or animal subject, it is common to introduce a cryogenic liquid, for example, liquid nitrogen, into the cavity. For example, in the cryogenic treatment of cells, for example, cancer cells, tumours and the like, cryogenic liquid, such as liquid nitrogen is directed to the cells or tumour which are to be treated, in order to freeze and in turn kill the cells or tumour. In the carrying out of such cryogenic procedures, it is normal to insufflate the cavity in which the treatment is to be carried out prior to the introduction of the cryogenic liquid. However, on introduction of the cryogenic liquid into the cavity, the cryogenic liquid rapidly converts to gas and expands at a rapid rate, and thus, must be removed in order to avoid over pressurising the cavity, which would result in rupturing or other damage to the cavity in which the procedure is being carried out. In general, a vacuum is applied to the cavity just prior to the introduction of the cryogenic liquid. However, this, in general, results in the collapse of the cavity prior to the introduction of the cryogenic liquid, which is undesirable, since once the cavity has collapsed, it is no longer possible to direct the cryogenic liquid to the specific site at which the cells or tumour to be treated are located.

There is therefore a need for a method and apparatus which addresses at least one of these problems.

The present invention is directed towards providing a method and apparatus for insufflating a cavity in the body of a human or animal subject which addresses at least one of these problems.

According to the invention there is provided apparatus for insufflating a cavity of a human or animal subject during a procedure being carried out in the cavity, the apparatus comprising a delivery means for delivering an insufflating fluid to the cavity, a discharge control means for controlling the flow of insufflating fluid from the cavity, and a pressure monitoring means configured to monitor a pressure of the insufflating fluid indicative of the pressure of the insufflating fluid in the cavity, one of a flow control means and the discharge control means being responsive to one of the pressure monitoring means and an externally generated control signal for maintaining the pressure of the insufflating fluid in the cavity at a substantially constant predefined working pressure.

In one aspect of the invention the discharge control means is responsive to the one of the externally generated control signal and the pressure in the cavity exceeding a predefined maximum pressure for increasing the discharge of insufflating fluid from the cavity.

In another aspect of the invention the externally generated control signal comprises one of a manually generated signal, a signal generated in response to operation of an instrument in the cavity, a signal derived from a control system operating the instrument in the cavity indicative of one of the operation and commencement of operation of the instrument.

In another aspect of the invention the discharge control means is operable for maximising discharge of insufflating fluid from the cavity in response to one of the externally generated signal and the pressure in the cavity exceeding the predefined maximum pressure.

In a further aspect of the invention a timing means is provided for timing a predefined time period in response to one of the signal generated in response to operation of an instrument in the cavity and the signal derived from a control system operating the instrument in the cavity being indicative of one of the commencement of the operation of the instrument in the cavity and the ceasing of operation of the instrument therein.

Preferably, the discharge control means is operable for reducing discharge of the insufflating fluid from the cavity in response to one of the absence of the manually generated signal, one of the signal generated in response to operation of the instrument in the cavity and the signal derived from a control system operating the instrument in the cavity being indicative of ceasing of operation of the instrument in the cavity and the timer having timed out the predefined time period.

Advantageously, the discharge control means is operable for minimising discharge of the insufflating fluid from the cavity in response to one of the absence of the manually generated signal, one of the signal generated in response to operation of the instrument in the cavity and the signal derived from the control system operating the instrument in the cavity being indicative of ceasing of operation of the instrument in the cavity and the timer having timed out the predefined time period.

Preferably, the flow control means is responsive to the pressure in the cavity falling below the predefined working pressure for increasing the flow rate of the insufflating fluid to the cavity. Advantageously, the flow control means is responsive to the pressure in the cavity exceeding the predefined maximum pressure for shutting off the insufflating fluid to the cavity. Ideally, the flow control means is responsive to the pressure of the insufflating fluid in the cavity monitored by the pressure monitoring means exceeding the predefined working pressure for shutting off the supply of the insufflating fluid to the cavity.

Preferably, the predefined maximum pressure is selectable. Advantageously, the predefined working pressure is selectable. Preferably, the predefined time is selectable.

In one aspect of the invention the discharge control means comprises a discharge control valve alternately and selectively operable in a first state fully open, and a second state fully closed. Preferably, the discharge control valve comprises a bi-state valve. Advantageously, the discharge control valve comprises one of an electrically operated and a pneumatically operated valve. Ideally, the discharge control valve comprises a solenoid operated valve.

Preferably, the discharge control valve comprises a variable state valve.

In another aspect of the invention the discharge control means comprises a vacuum pump.

Preferably, a filter is provided for filtering insufflating fluid being discharged from the cavity. Advantageously, the filter is located adjacent a downstream end of the discharge control means.

In one aspect of the invention the pressure monitoring means is configured for locating in or adjacent the cavity.

In another aspect of the invention the pressure monitoring means is configured for locating externally of the cavity, and communicates with the cavity through a conduit in which the fluid in the conduit is a static fluid.

In another aspect of the invention the flow control means comprises a variable state valve. Advantageously, the flow control means comprises a motor control valve.

In another aspect of the invention the flow control valve comprises one of an electric motor controlled valve and a pneumatic motor controlled valve.

In a further aspect of the invention an input communicating conduit is provided for communicating the flow control means with the cavity.

In another aspect of the invention an output communicating conduit is configured for communicating the discharge control means with the cavity.

Preferably, the input communicating conduit terminates in an inlet port to which the insufflating fluid is delivered into the cavity. Advantageously, the inlet port is located in a first trocar.

In a further aspect of the invention the output communicating conduit and the input communicating conduit are configured as a single communicating conduit having a single bore extending therethrough for alternately accommodating the flow of the insufflating fluid in respective opposite direction therethrough to and from the cavity.

Preferably, the single communicating conduit terminates at a proximal end in a two way connecting element for connecting to the flow control means and the discharge control means, respectively. Advantageously, the single communicating conduit terminates in a distal end configured for extending into the cavity.

In another aspect of the invention the discharge control means is located on or adjacent a second trocar.

In another aspect of the invention the output communicating conduit connects the discharge control means to the two-way connecting element.

In one aspect of the invention the insufflating fluid comprises an insufflating gas. Preferably, the insufflating gas comprises one of air, carbon dioxide and an inert gas.

In one aspect of the invention the predefined working pressure lies in the range of 5 mmHg to 15 mmHg. Preferably, the predefined working pressure lies in the range of 10 mmHg to 15 mmHg. Advantageously, the predefined working pressure is approximately 15 mmHg.

In one aspect of the invention the predefined maximum pressure lies in the range of 15 mmHg to 30 mmHg. Preferably, the predefined maximum pressure lies in the range of 20 mmHg to 30 mmHg. Advantageously, the predefined maximum pressure is approximately 20 mmHg.

In one aspect of the invention a control means is provided for controlling the operation of the flow control means and the discharge control means.

In another aspect of the invention the control means is responsive to the one of the externally generated control signals and the pressure in the cavity exceeding the predefined maximum pressure for operating the one of the flow control means and the discharge control means.

In a still further aspect of the invention the control means comprises a microcontroller.

In one aspect of the invention the apparatus is configured for controlling the pressure in a cavity of a human or animal subject during a laparoscopic procedure.

The invention also provides apparatus for removing an undesirable gas from a cavity in the body of a human or animal subject during a procedure, such as a laparoscopic procedure, the apparatus comprising a delivery means for delivering an insufflating fluid to the cavity, a discharge control means for controlling the flow of the insufflating fluid from the cavity to remove the undesirable gas, a pressure monitoring means for monitoring a pressure of the insufflating fluid indicative of the pressure of the insufflating fluid in the cavity, and a flow control means responsive to the pressure monitoring means for controlling the flow rate of the insufflating fluid to the cavity in response to the pressure monitoring means to maintain the pressure of the insufflating fluid in the cavity at a substantially constant predefined working pressure.

In one aspect of the invention the discharge control means is selectively and alternately operable in a first state for minimising discharge of the insufflating fluid from the cavity, and a second state for permitting flow of the insufflating fluid from the cavity to remove the undesirable gas therefrom.

Preferably, the discharge control means is operable from the first state to the second state in response to one of a first electrical control signal and a first pneumatic control signal, and the discharge control means is operable from the second state to the first state in response to one of a second electrical control signal and a second pneumatic control signal.

Advantageously, the first control signal comprises one of a manually generated signal, a signal generated in response to operation of an instrument in the cavity and a signal derived from a control system operating an instrument in the cavity indicative of one of the operation of the instrument and the commencement of operation of the instrument.

In another aspect of the invention a timer is provided for timing a predefined time period in response to one of the first control signal and the signal derived from a control system operating an instrument in the cavity being indicative of operation of the instrument ceasing.

Preferably, the second control signal comprises one of a manually generated signal, the one of the signal generated in response to operation of an instrument in the cavity and the signal derived from the control system operating an instrument in the cavity being indicative of operation of the instrument in the cavity ceasing, and the timer timing out the predefined time period.

In one aspect of the invention the manually generated first control signal is generated by an electrical switch. Preferably, the second control signal is generated by the electrical switch.

In one aspect of the invention the electrical switch comprises a foot pedal operated switch. Alternatively, the electrical switch comprises a hand operated switch.

In one aspect of the invention the discharge control means comprises one of a discharge control valve and a vacuum pump.

In another aspect of the invention the discharge control valve comprises a bi-state discharge control valve. Preferably, the discharge control valve in the first state is operable in a closed state, and in the second state is operable in a fully opened state. Advantageously, the discharge control valve is configured so that in the first state the discharge control valve permits leakage therethrough. Ideally, the discharge control valve is a variable state valve.

In one aspect of the invention the discharge control valve is one of electrically and pneumatically controlled.

Preferably, the discharge control valve comprises a solenoid operated valve.

Advantageously, a filter is provided for filtering the insufflating fluid being discharged by the discharge control means. Preferably, the filter is located downstream of the discharge control means.

In another aspect of the invention the pressure monitoring means is configured for locating in or adjacent the cavity.

In one aspect of the invention the pressure monitoring means is configured for locating externally of the cavity and communicating with the cavity through a conduit, in which the fluid in the conduit is a static fluid.

In another aspect of the invention the flow control means comprises a variable state valve. Preferably, the flow control means comprises a motor controlled valve.

In one aspect of the invention the flow control valve is controlled by one of an electric motor and a pneumatic motor.

In another aspect of the invention an inlet port configured for delivering the insufflating fluid into the cavity is provided, the inlet port being configured to receive the insufflating fluid from the flow control means.

Preferably, the inlet port is configured for locating in a trocar.

Advantageously, an outlet port is configured for accommodating insufflating fluid from the cavity, the discharge control means communicating with the outlet port.

In one aspect of the invention the outlet port is configured for locating in a trocar.

In a further aspect of the invention the outlet port is configured for locating in a different trocar to the trocar in which the inlet port is configured for locating.

In one aspect of the invention the pressure monitoring means is configured for monitoring the pressure in the cavity adjacent one of the trocars.

Preferably, the pressure monitoring means is located on one of the trocars. Advantageously, the pressure monitoring means is located on the trocar in which the inlet port is configured for locating therein. Alternatively, the pressure monitoring means is located on a trocar other than the trocar in which the inlet and outlet ports are located.

In another aspect of the invention the pressure monitoring means is located in a Veress needle extending into the cavity.

Preferably, the pressure monitoring means is located adjacent a distal end of the Veress needle within the cavity.

In an alternative aspect of the invention the pressure monitoring means is located remotely of the cavity in a conduit extending from the Veress needle in which a static fluid is located, so that the pressure being monitored by the pressure monitoring means is substantially identical to the pressure of the insufflating fluid in the cavity.

In one aspect of the invention an electronic control means is provided for controlling the operation of the apparatus. Preferably, the electronic control means is configured for operating the discharge control means and the flow control means.

In one aspect of the invention the instrument comprises a surgical instrument, the use or operation of which generates smoke and/or other undesirable gases.

In another aspect of the invention the instrument comprises a cauterising instrument.

In a further aspect of the invention the electronic control means comprises a microcontroller.

In another aspect of the invention the discharge control means is operable in the second state in response to the pressure of the inflating medium in the cavity exceeding a predefined maximum pressure.

In a further aspect of the invention the flow control means is operated to shut off the insufflating fluid to the cavity in response to the pressure of the insufflating fluid in the cavity exceeding the predefined maximum pressure.

Preferably, an alerting means is provided, and the alerting means is configured to output a human sensory perceptible signal in response to the pressure in the cavity one of exceeding the predefined maximum pressure and falling below a predefined minimum pressure.

Preferably, the predefined working pressure is selectable. Advantageously, the predefined minimum pressure is selectable. Ideally, the predefined maximum pressure is selectable.

In one aspect of the invention the apparatus is configured for controlling the pressure in a cavity of a human or animal subject during a laparoscopic procedure.

In one aspect of the invention the predefined minimum pressure lies in the range of 5 mmHg to 15 mmHg. Preferably, the predefined minimum pressure lies in the range of 5 mmHg to 10 mmHg. Advantageously, the predefined minimum pressure is approximately 10 mmHg.

Additionally, the invention provides apparatus for insufflating a cavity in the body of a human or animal subject, the apparatus comprising a delivery means for delivering an insufflating fluid to the cavity, a discharge control means for evacuating fluid from the cavity, and a pressure monitoring means configured to produce a signal indicative of the pressure in the cavity, wherein the discharge control means is responsive to the signal produced by the pressure monitoring means being indicative of the pressure in the cavity exceeding one of a predefined maximum pressure and a predefined working pressure for evacuating the cavity to reduce the pressure therein.

In one aspect of the invention the discharge control means is responsive to the signal produced by the pressure monitoring means being indicative of the pressure in the cavity exceeding one of the predefined maximum pressure and the predefined working pressure for evacuating the cavity to reduce the pressure therein to one of the predefined working pressure and a pressure just below the predefined working pressure.

In another aspect of the invention the discharge control means is responsive to the signal produced by the pressure monitoring means being indicative of the pressure in the cavity falling to or just below the predefined working pressure to terminate evacuating of the cavity.

In another aspect of the invention the delivery means is responsive to the signal produced by the pressure monitoring means for maintaining the pressure in the cavity substantially constant at the predefined working pressure.

Preferably, the delivery means is responsive to the signal produced by the pressure monitoring means being indicative of the pressure in the cavity exceeding one of the predefined maximum pressure and the predefined working pressure for terminating insufflation of the cavity.

In another aspect of the invention the delivery means is responsive to the signal produced by the pressure monitoring means being indicative of the pressure in the cavity exceeding one of the predefined maximum pressure and the predefined working pressure for terminating insufflation of the cavity until the pressure therein returns to or just below the predefined working pressure.

Preferably, the delivery means is responsive to the signal produced by the pressure monitoring means being indicative of the pressure falling to or just below the predefined working pressure for delivering the insufflating fluid to the cavity.

In one aspect of the invention the delivery means comprises a flow control means for controlling the flow of the insufflating fluid to the cavity.

In another aspect of the invention the flow control valve comprises one of a solenoid operated valve and a motor controlled valve. Preferably, the motor controlled valve comprise a multi-state valve.

In one aspect of the invention the discharge control means comprises one of a discharge control valve and a vacuum pump.

In another aspect of the invention the discharge control valve comprises an exhaust valve. Preferably, the exhaust valve comprises a bi-state exhaust valve.

Advantageously, the bi-state exhaust valve is selectively and alternatively operable in a closed state and a fully open state. Preferably, the exhaust valve is operable in at least one intermediate state between the fully open state and the closed state.

In another aspect of the invention the exhaust valve is configured in the intermediate state to provide controlled leakage of insufflating fluid from the cavity.

In another aspect of the invention an input communicating conduit is provided for communicating the delivery means with the cavity. Preferably, the input communicating conduit is configured for communicating with the cavity through an endoscope or alongside an endoscope but externally thereof. Advantageously, the input communicating conduit is configured for communicating with the cavity through a first trocar. Preferably, the input communicating conduit is configured to communicate with an inlet port located in the first trocar.

In another aspect of the invention an output communicating conduit is provided for communicating the discharge control means with the cavity. Preferably, the output communicating conduit is configured for communicating with the cavity through an endoscope or alongside the endoscope and externally thereof. Advantageously, the output communicating conduit is configured to communicate with the cavity through a second trocar. Preferably, the output communicating conduit is configured to communicate with an output port located in the second trocar.

In one aspect of the invention the input and output communicating conduits communicate with a single communicating conduit configured to extend into the cavity.

Preferably, the single communicating conduit is configured to extend into the cavity through one of the first and second trocars and the endoscope or alongside the endoscope but externally thereof.

In one aspect of the invention the discharge control means is located on the second trocar.

In another aspect of the invention the vacuum pump is coupled to the outlet port through the output communicating conduit.

In a further aspect of the invention the pressure monitoring means is located in the cavity. Alternatively, the pressure monitoring means is located externally of the cavity and communicates with the cavity for monitoring the static pressure in the cavity. Preferably, the pressure monitoring means communicates with the cavity through a conduit having a static fluid therein.

In one aspect of the invention the pressure monitoring means comprises a pressure sensor.

In another aspect of the invention a control means is provided for controlling the delivery means and the discharge control means, and the control means is responsive to signals read from the pressure monitoring means for controlling the delivery means and the discharge control means.

Preferably, the predefined maximum pressure is selectable. Advantageously, the predefined working pressure is selectable.

In one aspect of the invention the insufflating fluid is derived from a pressurised source of the insufflating fluid. Preferably, the insufflating fluid comprises an insufflating gas. Advantageously, the insufflating gas comprises one of compressed air, compressed carbon dioxide and an inert compressed gas.

In one aspect of the invention the insufflating pressurised carbon dioxide is derived from a pressurised vessel containing the carbon dioxide in pressurised liquid form.

In another aspect of the invention the apparatus is configured for controlling the pressure in a cavity of a human or animal subject during a laparoscopic procedure.

Further the invention provides a method for insufflating a cavity of a human or animal subject during a procedure being carried out in the cavity, the method comprising delivering an insufflating fluid into the cavity, providing for discharge of the insufflating fluid from the cavity, monitoring a pressure of the insufflating fluid indicative of the pressure of the insufflating fluid in the cavity, controlling one of the flow of insufflating fluid through the cavity and the discharge of insufflating fluid from the cavity in response to one of the pressure of the insufflating fluid in the cavity and an externally generated control signal for maintaining the pressure of the insufflating fluid in the cavity at a predefined working temperature.

In one aspect of the invention insufflating fluid is discharged from the cavity in response to the pressure of the insufflating fluid in the cavity exceeding one of the predefined working pressure and a predefined maximum pressure.

In another aspect of the invention insufflating fluid is discharged from the cavity in response to one of the predefined maximum pressure in the cavity exceeding the predefined maximum pressure and the externally generated control signal.

In one aspect of the invention the externally generated control signal comprises one of a manually generated signal, a signal generated in response to operation of an instrument in the cavity, a signal derived from a control system operating an instrument in the cavity indicative of one of the operation of the instrument and the commencement of operation of the instrument.

Preferably, delivery of the insufflating fluid to the cavity is shut off in response to the pressure of the insufflating fluid in the cavity exceeding one of the predefined maximum pressure and the predefined working pressure. Advantageously, delivery of the insufflating fluid to the cavity is shut off in response to the pressure of the insufflating fluid in the cavity exceeding the predefined maximum pressure.

In one aspect of the invention delivery of the insufflating fluid to the cavity is shut off in response to the pressure of the insufflating fluid in the cavity exceeding the predefined working pressure.

In another aspect of the invention delivery of the insufflating fluid to the cavity is increased in response to the pressure of the insufflating fluid in the cavity falling below the predefined working pressure for maintaining the pressure in the cavity at the predefined working pressure.

Preferably, delivery of the insufflating fluid to the cavity is controlled by a flow control means.

In one aspect of the invention the flow control means comprises a flow control valve.

In another aspect of the invention discharge of the insufflating fluid from the cavity is controlled by a discharge control means.

In a further aspect of the invention the discharge control means comprises one of a discharge control valve and a vacuum pump.

In another aspect of the invention the insufflating fluid is delivered into the cavity through one of a trocar, an endoscope, or through an input communicating conduit extending alongside but externally of the endoscope.

In another aspect of the invention the method is configured for controlling the pressure in a cavity in human or animal subject during a laparoscopic procedure being carried out in the cavity.

The invention also provides a method for removing an undesirable gas from a cavity in the body of a human or animal subject during a procedure, the method comprising temporarily increasing the flow of an insufflating fluid being delivered to the cavity, for in turn temporarily increasing the flow rate of the insufflating fluid through the cavity for removing the undesirable gas.

In one aspect of the invention the flow rate of the insufflating fluid through the cavity is increased by increasing the rate through which the insufflating fluid is discharged from the cavity.

In another aspect of the invention the flow rate of the insufflating fluid is increased in response to the pressure in the cavity falling below a predefined working pressure.

In another aspect of the invention the method further comprises providing a discharge control means for controlling the flow of the insufflating fluid from the cavity to remove the undesirable gas and providing a pressure monitoring means for monitoring a pressure of the insufflating fluid indicative of the pressure of the insufflating fluid in the cavity, and increasing the delivery of the insufflating fluid to the cavity in response to the pressure in the cavity falling below the predefined working pressure.

In one aspect of the invention a flow control means is provided for controlling the flow of the insufflating fluid to the cavity, the flow control means being responsive to the pressure monitoring means for controlling the flow rate of the insufflating fluid to the cavity in response to the pressure monitored by the pressure monitoring means in order to maintain the pressure of the insufflating fluid in the cavity at the predefined working pressure.

In another aspect of the invention an inlet port configured for delivering the insufflating fluid into the cavity is provided, the inlet port being configured for receiving the insufflating fluid from the flow control means.

In another aspect of the invention an outlet port is configured for discharging the insufflating fluid from the cavity, and the discharge control means communicates with the outlet port.

Preferably, the discharge control means is selectively and alternately operable in a first state for minimising discharge of the insufflating fluid from the cavity, and in a second state for permitting flow of the insufflating fluid from the cavity to remove the undesirable gas therefrom.

Advantageously, the discharge control means is operable from the first state in response to one of a first externally generated electrical control signal and a first externally generated pneumatic control signal, and the discharge control means is operable into the first state in response to one of a second externally generated electrical control signal and a second externally generated pneumatic control signal.

In one aspect of the invention the first externally generated electrical control signal comprises one of a manually generated signal, a signal generated in response to operation of an instrument in the cavity, and a signal derived from a control system operating an instrument in the cavity indicative of one of the operation of the instrument and the commencement of operation of the instrument.

In another aspect of the invention a predefined time period is timed from the time that one of the signal generated in response to operation of an instrument in the cavity and the signal derived from a control system operating an instrument in the cavity is indicative of one of the commencement of operation of the instrument and ceasing of operation of the instrument.

In a further aspect of the invention the second externally generated electrical control signal comprises one of a manually generated signal, one of the signal generated in response to operation of an instrument in the cavity and the signal derived from a control system operating the instrument in the cavity being indicative of operation of an instrument in the cavity ceasing, and timing out of the predefined time period.

In another aspect of the invention the manually generated first control signal is generated by an electrical switch.

In another aspect of the invention the second control signal is generated by the electrical switch.

In another aspect of the invention the electrical switch comprises a foot pedal operated electrical switch. Alternatively, the electrical switch comprises a hand operated switch.

In one aspect of the invention the discharge control means comprises one of a discharge control valve and a vacuum pump.

In another aspect of the invention the insufflating fluid is filtered through a filter on discharge from the cavity. Preferably, the filter is located downstream of the discharge control means.

In another aspect of the invention the pressure monitoring means is configured for locating in or adjacent the cavity.

In another aspect of the invention the pressure monitoring means is located externally of the cavity and communicates with the cavity through a conduit in which the fluid in the conduit is static.

In a further aspect of the invention the flow control means comprises a variable state flow control valve.

In a further aspect of the invention the insufflating fluid comprises one of compressed air, compressed carbon dioxide and a compressed inert gas.

Preferably, the predefined working pressure is selectable.

In one aspect of the invention the instrument comprises an instrument, the operation of which results in the generation of smoke or an undesirable gas in the cavity.

Further the invention provides a method for insufflating a cavity of a human or animal subject during a procedure being carried out therein, the method comprising delivering an insufflating fluid to the cavity, monitoring a pressure of the insufflating fluid indicative of the pressure of the insufflating fluid in the cavity, discharging insufflating fluid from the cavity in response to the pressure in the cavity exceeding one of a predefined maximum pressure and a predefined working pressure, and terminating discharge of the insufflating fluid from the cavity on the pressure of the insufflating fluid in the cavity falling to or just below the predefined working pressure.

In one aspect of the invention delivery of the insufflating fluid to the cavity is terminated in response to the pressure of the insufflating fluid in the cavity exceeding the predefined maximum pressure.

In another aspect of the invention delivery of insufflating fluid to the cavity is terminated on the pressure in the cavity exceeding the predefined working pressure.

In another aspect of the invention the delivery of the insufflating fluid to the cavity is recommenced on the pressure of the insufflating fluid in the cavity falling to or just below the predefined working pressure.

In a further aspect of the invention delivery of the insufflating fluid to the cavity is controlled for maintaining the pressure of the insufflating fluid in the cavity substantially constant at the predefined working pressure.

In a further aspect of the invention insufflating fluid is discharged from the cavity by opening a discharge control valve configured for accommodating insufflating fluid from the cavity.

In another aspect of the invention insufflating fluid is discharged from the cavity by drawing the insufflating fluid from the cavity by a vacuum pump configured for communicating with the cavity.

Preferably, insufflating fluid is delivered to the cavity under the control of a flow control means. Preferably, the flow control means comprises a variable state flow control valve.

The advantages of the invention are many. The apparatus according to the invention rapidly removes gases, such as smoke and other gases which would inhibit the carrying out of a procedure in a cavity, in which tissue is being cauterised, with little or no loss of pressure of the insufflating fluid in the cavity during the removal of the smoke and other undesirable gases. By virtue of the fact that the discharge control means is initially operated to allow discharge of insufflating fluid and smoke and other gases from the cavity, and the flow control means is operated to increase the flow of insufflating fluid to the cavity in response to the subsequent decrease in pressure in the cavity, the flow of insufflating fluid through the cavity is rapidly increased, thereby resulting in the rapid removal of smoke and other undesirable gases, while at the same time avoiding any significant loss in the pressure of the insufflating fluid in the cavity.

A further advantage of the invention is that the apparatus according to the invention also rapidly removes gases resulting from a cryogenic procedure, and thereby avoids or minimises any danger of over-pressurising of the cavity. By virtue of the fact that the discharge control means is operated in response to the pressure of the insufflating fluid in the cavity exceeding a predefined maximum pressure for discharging or evacuating insufflating fluid from the cavity, the pressure of the insufflating fluid within the cavity is prevented from exceeding the predefined maximum pressure, and rapidly falls to the predefined working pressure without any danger of rupturing or other damage to the cavity in which the procedure is being carried out.

By providing the discharge control means as a vacuum pump particularly rapid evacuation of the cavity is achieved to thereby reduce the pressure of the insufflating fluid in the cavity to the predefined working pressure at which insufflating fluid is again delivered to the cavity, and the discharge control means is operated to reduce or minimise the flow of insufflating fluid from the cavity.

The advantages of the methods according to the invention are substantially similar to the advantages achieved by the apparatus according to the invention.

Figure 2:
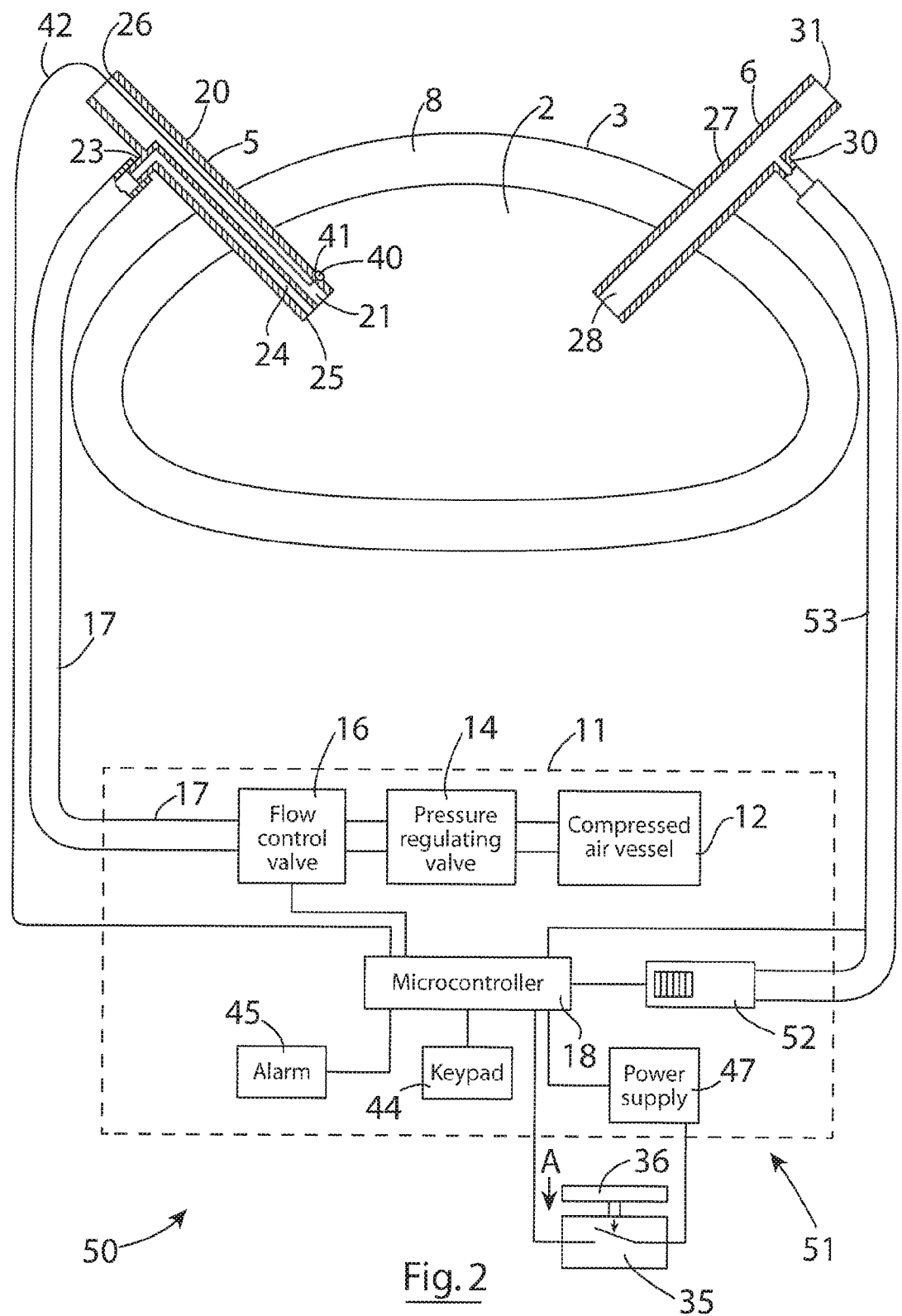
Figure 3:
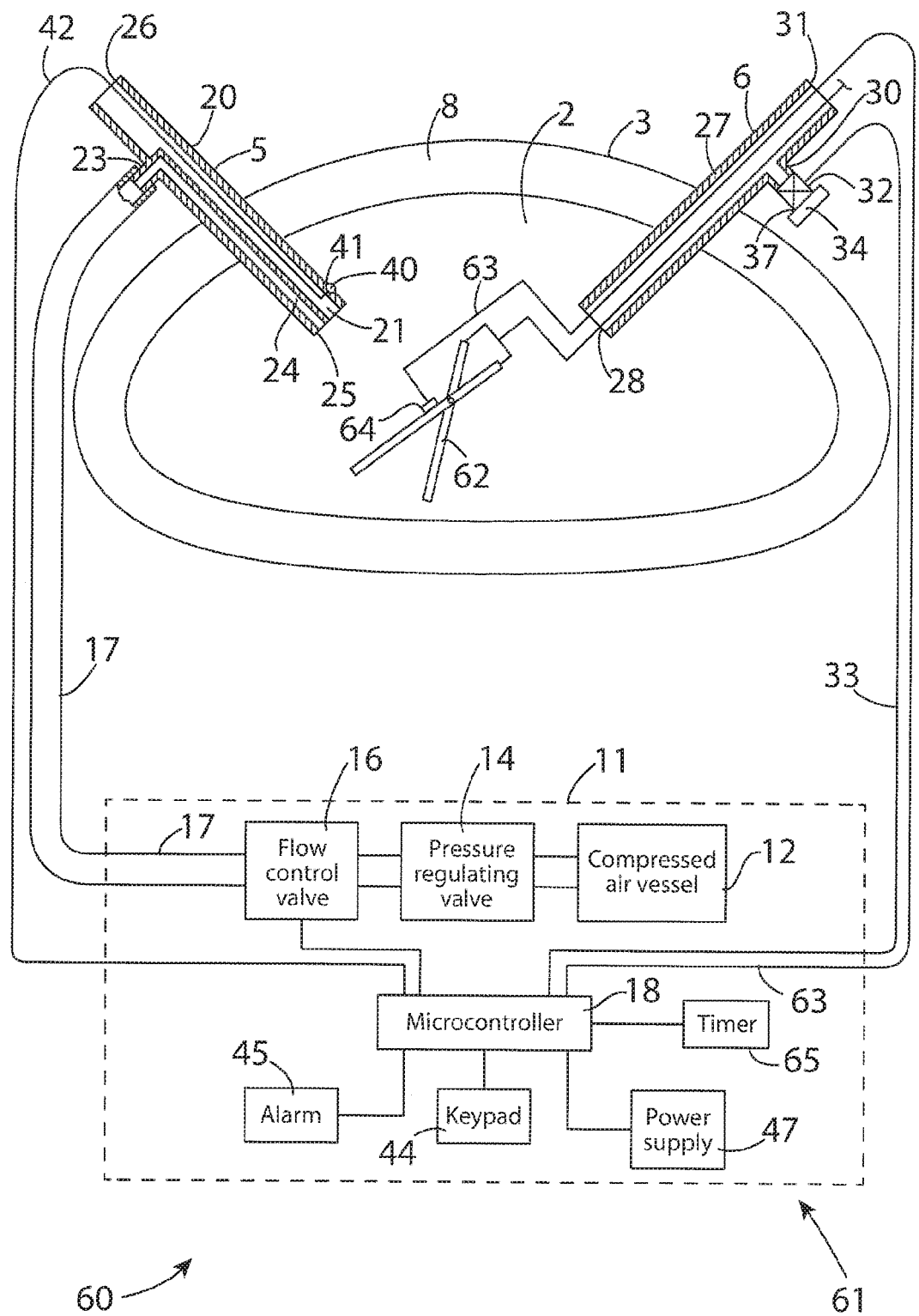
Figure 4:
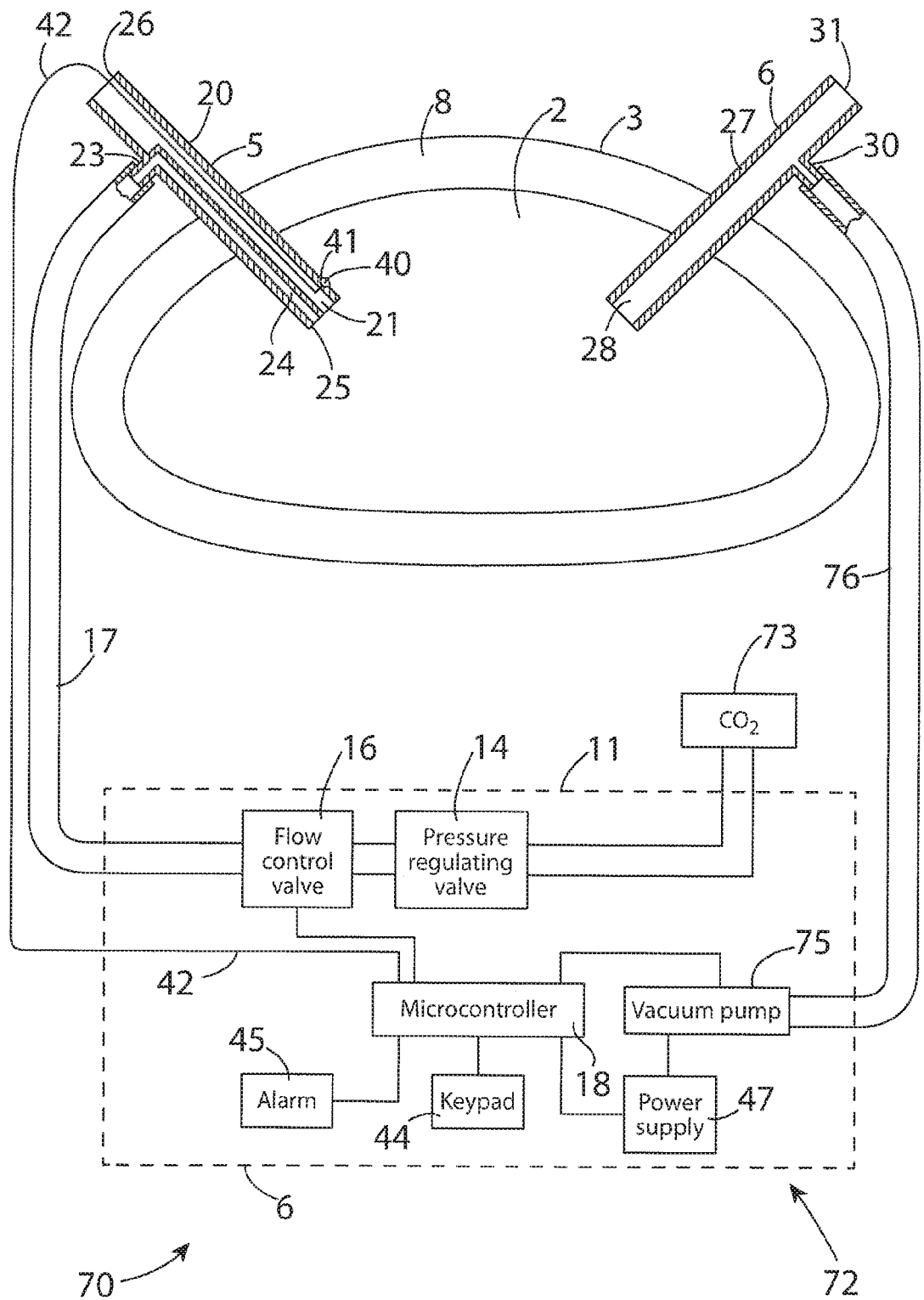
Figure 5:
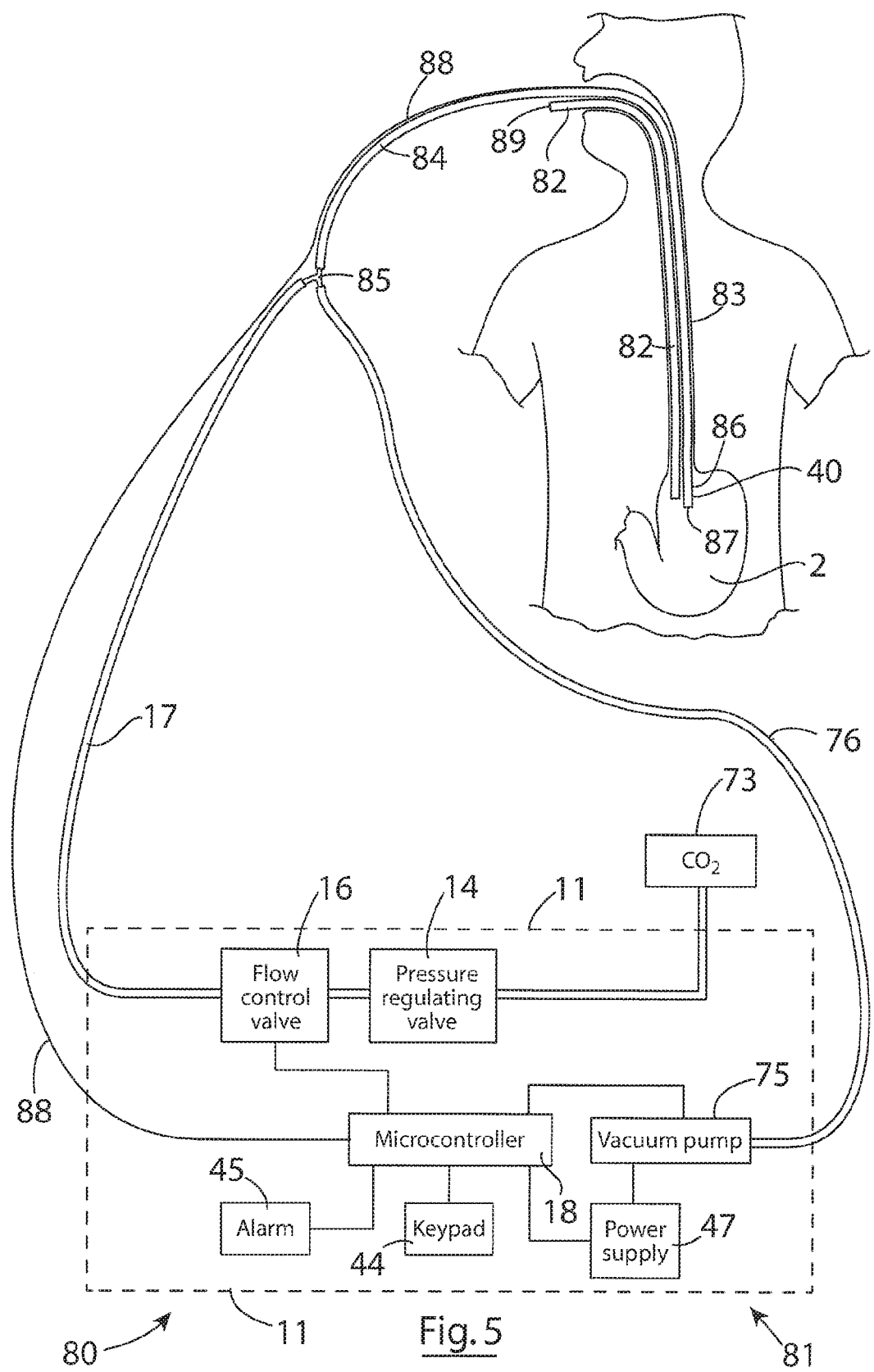
Figure 6:
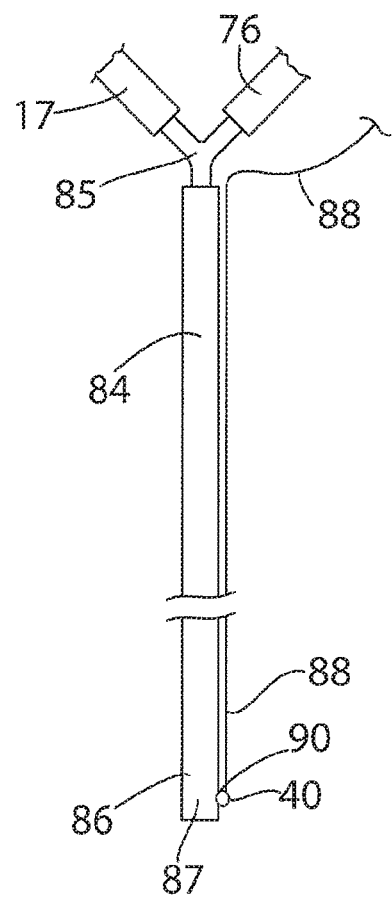
Figure 7:
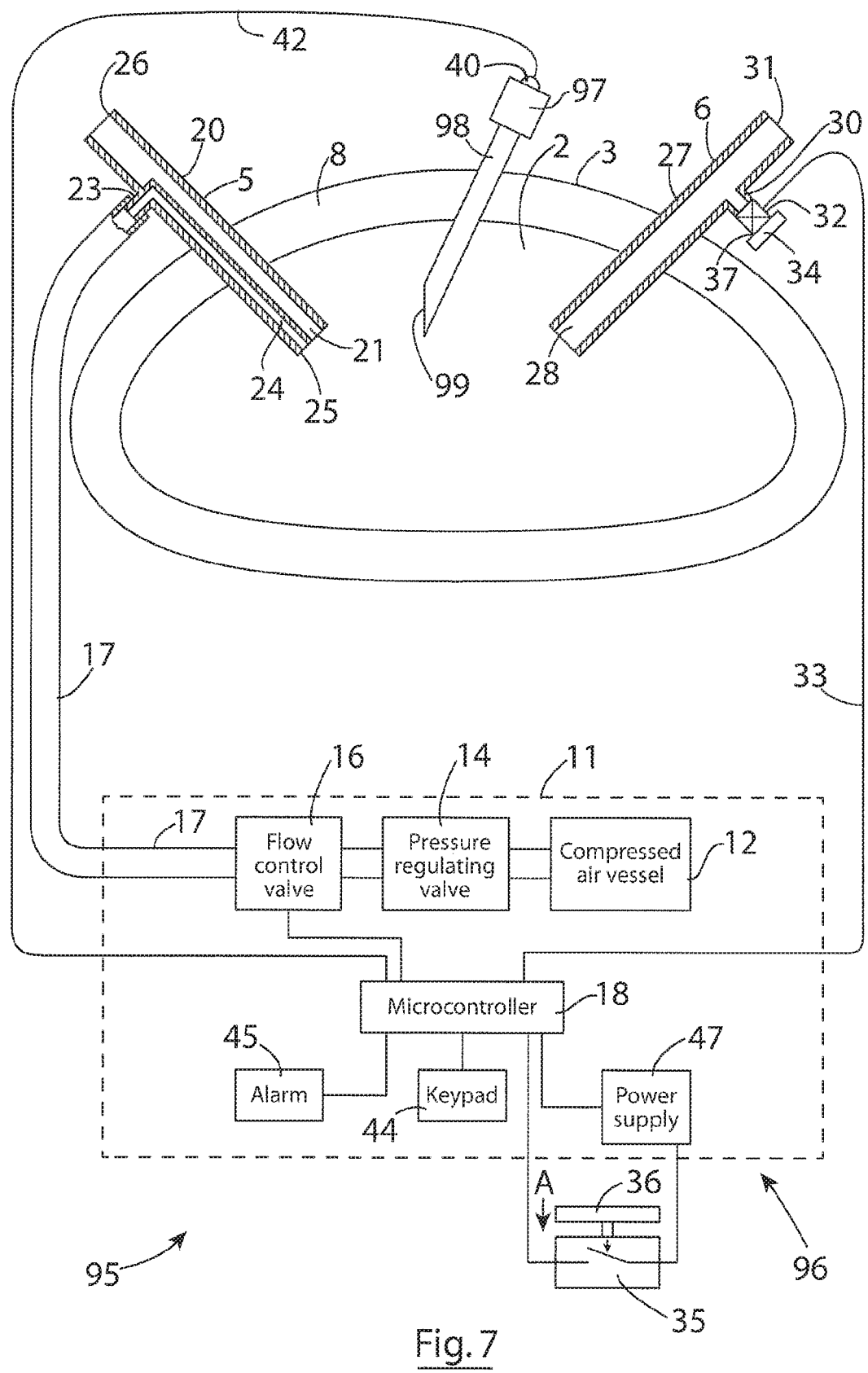

The invention will be more clearly understood by the following description of some preferred embodiments thereof, which are given by way of example only, with reference to the accompanying drawings, in which:

FIG. 1 is a schematic representation of apparatus according to the invention for insufflating a cavity in the body of a human or animal subject during for example, a laparoscopic procedure, FIG. 2 is a schematic representation of apparatus according to another embodiment of the invention also for insufflating a cavity in the body of a human or animal subject during, for example, a laparoscopic procedure, FIG. 3 is a schematic representation of apparatus according to a further embodiment of the invention for insufflating a cavity in the body of a human or animal subject during, for example, a laparoscopic procedure, FIG. 4 is a schematic representation of apparatus according to a further embodiment of the invention for insufflating a cavity in the body of a human or animal subject during, for example, a laparoscopic procedure, FIG. 5 is a schematic representation of apparatus according to another embodiment of the invention for insufflating a cavity in the body of a human or animal subject during a cryogenic procedure, FIG. 6 is an enlarged view of a detail of the apparatus of FIG. 5, and FIG. 7 is a schematic representation of apparatus according to another embodiment of the invention also for insufflating a cavity in the body of a human or animal subject during, for example, a laparoscopic procedure.

Referring to the drawings and initially to FIG. 1 thereof, there is illustrated apparatus according to the invention, indicated generally by the reference numeral 1, for insufflating a cavity 2 in the body 3 of a human or animal subject during a procedure, such as a laparoscopic procedure. In this embodiment of the invention the apparatus 1 is configured for removing smoke and other undesirable gases from the cavity 2 which would result from cauterising tissue or a vessel in the cavity 2. In this embodiment of the invention the cavity 2 is the peritoneal cavity of the subject. However, for convenience the organs, and those organs on which the procedure is being carried out during the laparoscopic procedure are not illustrated, but will be readily known to those skilled in the art. In general, during a laparoscopic procedure a number of trocars are inserted into the cavity in which the laparoscopic procedure is being performed, and the use of such trocars in a laparoscopic procedure will be well known to those skilled in the art. However, only two of the trocars, namely, a first trocar 5 and a second trocar 6 are illustrated inserted through the abdominal wall 8 into the cavity 2. The first and second trocars 5 and 6 will be described in more detail below.

The apparatus 1 comprises an insufflator 10 for delivering an insufflating fluid, which in this embodiment of the invention comprises an insufflating gas, which in this case is compressed air for maintaining the cavity 2 insufflated. However, it will be readily understood by those skilled in the art that any suitable insufflating gas may be used, for example, compressed carbon dioxide or any other suitable compressed inert gas. The insufflator 10 comprises a housing 11, which is illustrated in broken lines only, and within which a compressed air vessel 12 is located to provide the source of the insufflating air. The compressed air vessel 12 would typically be provided along with an air compressor, which would maintain the compressed air within the compressed air vessel 12 at a suitable pressure. The insufflating air is delivered from the compressed air vessel 12 through a delivery means which in this embodiment of the invention comprises a pressure regulating valve 14 and a flow control means, namely, an electrically powered motorised flow control valve 16, both of which are located in the housing 11. The pressure regulating valve 14 is configured for stepping down the pressure of the compressed insufflating air to a working pressure suitable for insufflating the cavity 2. The pressure regulating valve 14 may be a single stage pressure step down valve, or may comprise two or more pressure step down stages, in which the pressure of the compressed air would be stepped down in sequential stages. The pressure regulated insufflating air is then delivered from the pressure regulating valve 14 to the flow control valve 16. The flow control valve 16 is operable for controlling the flow rate at which the insufflating air is delivered to the cavity 2.

An input communicating conduit, namely, a supply conduit 17 supplies the insufflating air from the flow control valve 16 to the cavity 2 through the first trocar 5 as will be described in more detail below.

An electronic control means comprising a microcontroller 18 also located in the housing 11 controls the operation of the insufflator 10 and controls the operation of the flow control valve 16 as will be described below for maintaining the pressure of the insufflating air within the cavity 2 at a substantially constant selectable predefined working pressure.

Turning now to the first trocar 5, the trocar 5 comprises a tubular member 20 through which an elongated bore 21 extends for accommodating surgical instruments, a surgical camera and the like, none of which are illustrated, into the cavity 2 as will be well known and understood by those skilled in the art. An inlet port 23 is located in the tubular member 20 for accommodating insufflating air into the cavity 2. The inlet port 23 is configured for connecting to the supply conduit 17 for receiving the insufflating air from the flow control valve 16 and delivering the insufflating air into the cavity 2. A delivery tube 24 from the inlet port 23 extends through the bore 21 of the first trocar 5 and terminates adjacent a distal end 25 of the first trocar 5 for delivering the insufflating air into the cavity 2. Alternatively, the inlet port 23 in the first trocar 5 may communicate directly with the bore 21 extending through the first trocar 5, and the insufflating air would be delivered from the inlet port 23 into the cavity directly through the bore 21 in the first trocar 5.

However, irrespective of how the insufflating air is delivered into the cavity 2 from the inlet port 23, a seal (not shown), in general, is provided in the bore 21 adjacent a proximal end 26 of the first trocar 5 to sealably co-operate with tubes, catheters, cables and other components extending through the bore 21 during a laparoscopic procedure in order to minimise leakage of insufflating air to atmosphere through the proximal end 26 of bore 21 of the first trocar 5. While the seal may be located at any suitable location in the bore 21 of the first trocar 5, in the event of the inlet port 23 communicating directly with the bore 21 of the first trocar 5, the seal would be provided in the trocar 5 upstream of the inlet port 23, between the inlet port 23 and the proximal end 26 of the trocar 5. The provision of such seals in the bore of a trocar will be well known to those skilled in the art.

Turning now to the second trocar 6, the second trocar 6 comprises a tubular member 27 having a bore 28 extending therethrough also for accommodating surgical instruments, a camera and the like into the cavity 2. An outlet port 30 is located in the tubular member 27 and communicates with the bore 28 for facilitating discharge of the insufflating air, smoke and other undesirable gases from the cavity 2. A discharge control means, which in this embodiment of the invention comprises a bi-state solenoid operated discharge control valve 32 is located in the outlet port 30. The discharge control valve 32 is selectively and alternately operable in a first state, namely, a fully closed state for minimising discharge of the insufflating air from the cavity 2, and a second state, namely, a fully open state for facilitating discharge of insufflating air from the cavity 2, in order to facilitate an increase in the flow of insufflating air from the cavity 2 for removal of the smoke and other undesirable gases from the cavity 2. As described with reference to the first trocar 5, a seal (not shown), in general, is also provided in the second trocar 6 for co-operating with tubes, catheters, cables and other components extending through the bore 28 of the second trocar 6 during a laparoscopic procedure for minimising leakage of insufflating air through the bore 28 of the second trocar 6. In this case, the seal is provided in the bore 28 upstream of the outlet port 30, between the outlet port 30 and a proximal end 31 of the second trocar 6, as will be understood by those skilled in the art.

However, even in cases where a seal is not provided in either or both of the trocars 5 and/or 6, in general, it would be expected that the flow control valve 16 will be controlled for compensating for leaks from the trocars 5 and 6 through the bores 21 and 28 thereof between the trocars 5 and 6 and the instruments extending through the bores 21 and 28. In general, in cases where the outer diameter of the instrument is reasonably similar to the inner diameter of the bore 21 or 28, or in cases where the sum of the cross-sectional areas of the instruments passing through one of the trocars 5 or 6 is reasonably similar to the cross-sectional area of the bore 21 or 28 extending through the corresponding one of the trocars 5 or 6, such seals may be omitted from the bores 21 and 28 of the trocars 5 and 6.

The discharge control valve 32 is operated under the control of the microcontroller 18 through an electrically conductive cable 33 between the first and second states. A first signal from the microcontroller 18 operates the discharge control valve 32 from the first state to the second state, while a second signal from the microcontroller 18 operates the discharge control valve 32 from the second state to the first state. In this embodiment of the invention the microcontroller 18 is responsive to externally and manually generated control signals for operating the discharge control valve 32 between the first and second states, which in this case are produced in response to the state of an electrical switch 35 which is operated by a foot pedal 36 for determining the required state of the discharge control valve 32.

The switch 35 comprises a bi-state mono-stable normally open circuit micro-switch, which on downward depression of the foot pedal 36 in the direction of the arrow A is operated from the normally open circuit state to the closed circuit state to produce a first control signal, and on release of pressure on the foot pedal 36, the switch 35 is spring returned from the closed circuit state to the normally open circuit state by a spring (not shown) to produce a second control signal. Thus, when it is desired to operate the discharge control valve 32 from the first state to the second state, the foot pedal 36 is depressed to produce the first control signal which is read by the microcontroller 18. The microcontroller 18 then in turn outputs the first signal to the discharge control valve 32 for operating the discharge control valve 32 from the first state to the second state. The microcontroller 18 maintains the discharge control valve 32 in the second state for so long as the switch 35 is maintained in the closed circuit state. On the switch 35 returning to the normally open circuit state, thereby producing the second control signal, the microcontroller 18 outputs the second signal to the discharge control valve 32 for operating the discharge control valve 32 from the second state to the first state.

A filter 34 is located in an outlet 37 from the discharge control valve 32 for filtering smoke and other undesirable gases from the insufflating air as they are discharged with insufflating air through the discharge control valve 32.

A pressure monitoring means, in this embodiment of the invention a piezoelectric pressure sensor 40 is located in a recess 41 formed in the outer surface the tubular member 20 of the first trocar 5 adjacent the distal end 25 thereof for monitoring the pressure of the insufflating air within the cavity 2. Although, it will be appreciated that any other suitable type pressure sensor may be used. An electrically conductive cable 42 connected to the pressure sensor 40 communicates the pressure sensor 40 with the microcontroller 18. The microcontroller 18 reads signals from the pressure sensor 40 for determining the pressure of the insufflating air in the cavity 2. The microcontroller 18 is programmed to operate the flow control valve 16 in response to signals read by the microcontroller 18 from the pressure sensor 40 being indicative of the pressure in the cavity 2 exceeding or falling below the predefined working pressure, for controlling the flow rate of the insufflating air to the cavity 2 in order to maintain the pressure of the insufflating air in the cavity 2 substantially constant at the predefined working pressure. The value of the predefined working pressure is selectable, and depending on the procedure being carried out, and the cavity within which the procedure is being carried out, is set, in general, in the range of 5 mm mercury to 20 mm mercury, and typically is set within the range 10 mm mercury to 15 mm mercury, and more typically, the predefined working pressure is set at a value of approximately 15 mm mercury.

On the discharge control valve 32 being operated into the second state in order to remove smoke and/or other undesirable gases from the cavity 2, the pressure of the insufflating air in the cavity 2 drops. On the signal read from the pressure sensor 40 by the microcontroller 18 being indicative of a drop of the pressure of the insufflating air in the cavity 2 below the predefined working pressure, the microcontroller 18 operates the flow control valve 16 to increase the flow rate of the insufflating air to the cavity 2, in order to maintain the pressure of the insufflating air in the cavity 2 at the predefined working pressure. The increase in the flow rate of the insufflating air to and through the cavity 2, and in turn through the discharge control valve 32 removes the smoke and other undesirable gases from the cavity 2 through the discharge valve 32.

An interface means, in this embodiment of the invention an interface keypad 44 is provided in the housing 11 to permit inputting data to the microcontroller 18, in particular, for inputting the selected predefined working pressure at which the insufflating air is to be maintained in the cavity 2.

An alerting means, in this case a piezoelectric sounder 45 is located in the housing 11. The microcontroller 18 is programmed to operate the piezoelectric sounder 45 to produce an audible alarm in response to the signals read from the pressure sensor 40 being indicative of the pressure of the insufflating air in the cavity exceeding a selectable predefined maximum pressure or falling below a selectable predefined minimum pressure. Additionally, the microcontroller 18 is programmed to operate the discharge control valve into the second state in response to the pressure of the insufflating air in the cavity 2 exceeding the predefined maximum pressure, and also to operate the flow control valve 16 to shut off the supply of insufflating air to the cavity 2 in response to the pressure of the insufflating air in the cavity 2 exceeding the predefined maximum pressure. The microcontroller 18 is also programmed to operate the discharge control valve 32 into the first state in response to the pressure of the insufflating air in the cavity 2 falling below the predefined minimum pressure, and also to operate the flow control valve 16 to increase the flow rate of insufflating air to the cavity 2. Both the selectable predefined maximum pressure and the selectable predefined minimum pressure are entered into the microcontroller 18 through the interface keypad 44. The values of the predefined maximum pressure and the predefined minimum pressure are selected depending on the procedure being carried out and the cavity within which the procedure is being carried out. Typically, the predefined maximum pressure is set at a value in the range of 15 mm mercury and 30 mm mercury and more typically in the range of 20 mm mercury to 30 mm mercury, and, in general, is set at a value of approximately 20 mm mercury. Typically, the predefined minimum pressure is set at a value in the range of 5 mm mercury to 10 mm mercury, and, in general, is set at a value of approximately 5 mm mercury.

A power supply 47 powers the insufflator 10.

In use, with the first and second trocars 5 and 6 inserted through the abdominal wall 8 into the cavity 2, and with the supply conduit 17 connecting the flow control valve 16 to the inlet port 23 of the trocar 5, and the cable 42 from the pressure sensor 40 connected to the microcontroller 18, and with the cable 33 connecting the discharge control valve 32 to the microcontroller 18, the apparatus 1 is ready for use. The predefined working pressure is entered into the microcontroller 18 through the keypad 44, and in this case the predefined working temperature is 15 mm mercury. The predefined maximum and minimum pressures are also entered into the microcontroller 18 through the keypad 44, and in this case, the predefined maximum pressure is set at 20 mm mercury, and the predefined minimum pressure is set at 10 mm mercury. However, it will be readily appreciated by those skilled in the art that depending on the procedure and the cavity in which the procedure is being carried out the predefined working pressure could range anywhere between 5 mm mercury to 20 mm mercury, and preferably, between 10 mm mercury and 15 mm mercury. The predefined maximum pressure could lie anywhere in the range of 15 mm mercury to 30 mm mercury, and preferably, between 20 mm mercury and 30 mm mercury. The predefined minimum pressure may lie anywhere in the range of 5 mm mercury to 10 mm mercury.

During normal operation of the apparatus 1 in the carrying out of a laparoscopic procedure, the discharge control valve 32 is operated under the control of the microcontroller 18 in the first state. The microcontroller 18 reads signals from the pressure sensor 40 and determines the pressure of the insufflating air in the cavity 2 from the signals read from the pressure sensor 40. The microcontroller 18 in response to the signals read from the pressure sensor 40 operates the flow control valve 16 for controlling the flow rate of insufflating air to the cavity 2 in order to maintain the pressure of the insufflating air in the cavity 2 substantially constant at the predefined working pressure.

As will be understood by those skilled in the art, during a laparoscopic procedure some insufflating air will normally leak through the bores 21 and 28 of the first and second trocars 5 and 6 used in the laparoscopic procedure, even though seals are provided in the bores 21 and 28 of the first and second trocars 5 and 6 for sealing against catheters, tubes, cables and other components which extend through the trocars into the cavity 2 during the laparoscopic procedure. Additionally, leakage of insufflating air occurs around the outer surface of the trocars 5 and 6 between the trocars and the abdominal wall or other wall through which the trocar is inserted into the cavity. Such leakage is particularly common around the outer surface of trocars through which surgical instruments are being manipulated as the surgeon manipulates those instruments in the cavity in which the procedure is being carried out. The microcontroller 18 controls the flow control valve 16 to in turn control the flow rate of the insufflating air to the cavity 2 to compensate for this loss in the insufflating air, so that the pressure of the insufflating air in the cavity 2 is maintained substantially constant at the predefined working pressure.

In the event of a cauterising instrument or other instrument which results in the generation of smoke or other undesirable gases being used by a surgeon in the laparoscopic procedure, the surgeon depresses the foot pedal 36, thereby operating the switch 35 from the normally open circuit state to the closed circuit state to produce the first control signal. The microcontroller 18 in response to the first control signal from the switch 35 outputs the first signal to the discharge control valve 32 for operating the discharge control valve 32 from the first state to the second state. With the discharge control valve 32 in the second state, the pressure of the insufflating air in the cavity 2 immediately commences to drop below the predefined working pressure, and on the microcontroller 18 detecting the drop in pressure in the cavity 2 from the signals read from the pressure sensor 40, the microcontroller 18 operates the flow control valve 16 to increase the flow rate of the insufflating air to the cavity 2 in order to maintain the pressure of the insufflating air in the cavity 2 substantially constant at the predefined working pressure. This in turn increases the flow rate of insufflating air through the discharge control valve 32 and in turn through the cavity 2. The increased flow rate of insufflating air through the cavity 2 rapidly removes any smoke and other undesirable gases generated by the cauterising procedure from the cavity 2.

When the surgeon is satisfied that the smoke and other undesirable gases have been removed from the cavity 2, the surgeon removes his foot from the foot pedal 36 to produce the second control signal, in response to the switch 35 transitioning from the closed circuit state to the open circuit state. On the microcontroller 18 detecting the second control signal, the microcontroller 18 outputs the second signal to the discharge control valve 32 for in turn operating the discharge control valve 32 from the second state to the first state. As the signals from the pressure sensor 40 read by the microcontroller 18 are indicative of the pressure in the cavity raising above the predefined working pressure as a result of the discharge control valve 32 being operated into the first state, the microcontroller 18 operates the flow control valve 16 to reduce the flow rate of the insufflating air to the cavity 2 to maintain the pressure in the cavity 2 at the predefined working pressure.

During the laparoscopic procedure, each time the cauterising instrument or other relevant instrument is operated by the surgeon, which generates smoke or other undesirable gases, the surgeon depresses the foot pedal 36 and retains the foot pedal 36 depressed until smoke or other undesirable gases resulting from cauterisation have been removed from the cavity 2.

In the event of the signals from the pressure sensor 40 read by the microcontroller 18 being indicative of the pressure in the cavity 2 exceeding the predefined maximum pressure, the microcontroller 18 operates the piezoelectric sounder 45 to output the audible alarm signal, and also operates the discharge control valve 32 into the second state and operates the flow control valve 16 to shut off the flow of insufflating air to the cavity 2 until the pressure of the insufflating air in the cavity 2 falls to or just below the predefined working pressure, at which stage the microcontroller operates the discharge control valve 32 into the first state, and the flow control valve 16 is then operated for supplying the insufflating air to the cavity 2 for maintaining the pressure of the insufflating air in the cavity 2 at the predefined working pressure. In the event of the signal read by the microcontroller 18 from the pressure sensor 40 being indicative of the pressure of the insufflating air in the cavity 2 falling to or just below the predefined minimum pressure, the microcontroller 18 operates the piezoelectric sounder 45 to produce an audible alarm signal. Additionally, if the discharge control valve 32 is in the second state, the microcontroller 18 operates the discharge control valve 32 from the second state to the first state and operates the flow control valve 16 to increase the flow of insufflating air to the cavity 2 in order to increase the pressure of the insufflating air in the cavity 2 to the predefined working pressure.

Referring now to FIG. 2, there is illustrated apparatus according to another embodiment of the invention, indicated generally by the reference numeral 50 for insufflating a cavity 2 of the body of a human or animal subject during a laparoscopic procedure, and for removing smoke and other desirable gases from the cavity during insufflating thereof. The apparatus 50 comprises an insufflator 51, and both the apparatus 50 and the insufflator 51 are substantially similar to the apparatus 1 and the insufflator 10 of FIG. 1, and similar components are identified by the same reference numerals. The main difference between the apparatus 50 and the apparatus 1 is that instead of the discharge control means being provided by the discharge control valve 32, the discharge control means comprises a vacuum pump 52 which is connected to the outlet port 30 from the second trocar 6 by a discharge conduit 53.

The vacuum pump 52 may be located in the housing 11 of the insufflator 51, or it may be attached to the second trocar 6 and communicate directly with the outlet port 30 from the second trocar 6, but in this embodiment of the invention the vacuum pump 52 is located in the housing 11. The vacuum pump 52 is operated under the control of the microcontroller 18 to draw insufflating air from the cavity 2 in response to signals read by the microcontroller 18 from the switch 35 which is operated by the foot pedal 36, and also in response to the signals read from the pressure sensor 40 by the microcontroller 18 being indicative of the pressure of the insufflating air in the cavity 2 exceeding the predefined maximum pressure.

On the microcontroller 18 detecting the first control signal from the switch 35 as the switch 35 is operated from the normal open circuit state into the closed circuit state, the microcontroller 18 outputs the first signal to activate the vacuum pump 52 to draw insufflating air from the cavity 2. Activation of the vacuum pump 52 results in a drop in the pressure in the cavity 2. On the signals read by the microcontroller 18 from the pressure sensor 40 being indicative of the pressure in the cavity 2 falling below the predefined working pressure, the microcontroller 18 operates the flow control valve 16 to increase the flow rate of the insufflating air to the cavity 2 to bring the pressure of the insufflating air in the cavity 2 up to the predefined working pressure, thereby increasing the flow of the insufflating air through the cavity 2 to remove smoke and other undesirable gases therefrom. The microcontroller 18 outputs a second signal to the vacuum pump 52 for deactivating the vacuum pump 52 in response to the second control signal from the switch 35 as the switch 35 transitioning from the closed circuit state to the open circuit state.

In this embodiment of the invention if the signals read by the microcontroller 18 from the pressure sensor 40 are indicative of the pressure in the cavity 2 reaching or just exceeding the predefined maximum pressure, the microcontroller 18 operates the piezoelectric sounder 45 to produce an audible alarm signal, and operates the vacuum pump 52 to draw insufflating air from the cavity 2 and also operates the flow control valve 16 to shut off the supply of insufflating air to the cavity 2, until the pressure of the insufflating air in the cavity 2 falls to or just below the predefined working pressure. At which stage the microcontroller 18 deactivates the vacuum pump 52, and operates the flow control valve 16 to maintain the pressure of the insufflating air in the cavity 2 at the predefined working pressure.

If the signals from the pressure sensor 40 read by the microcontroller 18 are indicative of the pressure in the cavity 2 falling below the predefined minimum pressure, the microcontroller 18 operates the piezoelectric sounder 45 to produce an audible alarm signal. Additionally, if the vacuum pump 52 is active, the microcontroller 18 deactivates the vacuum pump 52, and operates the flow control valve 16 to increase the supply of insufflating air to the cavity 2 in order to return the pressure in the cavity 2 to the predefined working pressure.

Otherwise, the apparatus 50 and the insufflator 51 are similar to the apparatus 1 and the insufflator 10, respectively, and there operation is also similar to that of the apparatus 1 and the insufflator 10.

Referring now to FIG. 3, there is illustrated apparatus according to another embodiment of the invention, indicated generally by the reference numeral 60 for insufflating a cavity 2 in the body 3 of a human or animal subject during a laparoscopic procedure, and also for removing smoke and other undesirable gases from the cavity 2 during insufflating thereof. The apparatus 60 comprises an insufflator 61, and both the apparatus 60 and the insufflator 61 are substantially similar to the apparatus 1 and the insufflator 10, and similar components are identified by the same reference numerals. The main difference between the apparatus 60 and the apparatus 1 is that operation of the discharge control valve 32 from the first state to the second state under the control of the microcontroller 18 is in response to a first externally generated control signal which is derived from operation of a cauterising instrument 62 or other relevant instrument in the cavity 2 which generates the smoke or other undesirable gas and a second externally generated control signal produced by a timer as will be described below.

A status monitoring means, namely, a status sensor 64 is provided on the cauterising instrument 62 or other relevant instrument, and produces signals indicative of the operational status of the cauterising or other instrument. The status sensor 64 is connected to the microcontroller 18 by an electrically conductive cable 63. The microcontroller 18 is programmed to read signals from the status sensor 64 and to determine the operational status of the cauterising instrument 62 or other relevant instrument from the signals read from the cauterising instrument. The cauterising instrument 62 is illustrated diagrammatically in FIG. 3, and the status sensor 64 is illustrated in block representation mounted on the cauterising instrument. Any suitable status monitoring sensor may be provided, for example, in the case of a cauterising instrument a pressure sensor element or a strain gauge which would detect pressure developing between the jaws of the cauterising instrument as the instrument is being operated.

Alternatively, the status sensor may comprise a voltage or a current sensor which would detect an electrical supply being applied to the cauterising instrument, thus indicating operation of the instrument. In the event that the status sensor is provided as a voltage or current sensor, the status sensor may be provided in the control system which controls operation of the cauterising or other instrument.

On the microcontroller 18 determining from signal read from the status sensor 64 that the signal is indicative of commencement of operation of the cauterising instrument 62 or other relevant instrument, the microcontroller 18 deems the signal read from the status sensor 64 to be a first control signal and the microcontroller 18 outputs the first signal to the discharge control valve 32 for operating the discharge control valve 32 from the first state to the second state.

A timer 65, which times a selectable predefined time period, is operated under the control of the microcontroller 18 to commence timing the predefined time period on the signal from the status sensor 64 being indicative of the termination of the operation of the cauterising instrument 62 or other relevant instrument. The duration of the predefined time period is selected to be of a sufficient duration to allow any remaining smoke or other undesirable gases remaining in the cavity 2 after termination of the cauterising process, to be removed from the cavity. On determining that the timer 65 has timed out the predefined time period, the microcontroller 18 deems the timing out of the predefined time period to be the second control signal, and the microcontroller 18 outputs the second signal to the discharge control valve 32 for operating the discharge control valve 32 from the second state to the first state. In this embodiment of the invention the predefined time period which the timer 65 is to be set to time, is inputted through the interface keypad 44 and typically would be in the range of 100 milliseconds to 20 seconds.

Alternatively, the timer 65 may be set to time the predefined time period from commencement of operation of the cauterising or other instrument and the duration of the predefined time period in this case would be selected to be of a duration which the surgeon would expect to require to complete the cauterising procedure, and to allow any residual smoke or other undesirable gases remaining in the cavity after completion of the cauterising process to be removed from the cavity 2. In which case, the microcontroller 18 on detecting the signal from the status sensor 64 of the cauterising instrument 62 being indicative of commencement of operation of the cauterising instrument 62, the microcontroller would output the first signal to the discharge control valve 32 for operating the discharge control valve 32 from the first state to the second state and would operate the timer 65 to commence timing the predefined time period. The microcontroller 18 would hold the discharge control valve 32 in the second state until the timer 65 had timed out the predefined time period, at which stage the microcontroller 18 would output the second signal to the discharge control valve 32 to operate the discharge control valve 32 from the second state to the first state.

It is also envisaged that the microcontroller 18 could be responsive solely to signals from the status sensor 64 of the cauterising instrument 62 and on the signal from the status sensor 64 being indicative of the commencement of operation of the cauterising instrument 62, the microcontroller 18 would output the first signal to the discharge control valve 32 to operate the discharge control valve 32 from the first state to the second state, and would then maintain the discharge control valve in the second state until the signal from the status sensor 64 was indicative of termination of the operation of the cauterising instrument 62. At which stage the microcontroller 18 would output the second signal to operate the discharge control valve 32 from the second state to the first state. It is envisaged that if the discharge control means were provided by a vacuum pump, such as the vacuum pump 52, deactivating the vacuum pump on termination of the operation of the cauterising instrument would most likely be sufficient for the removal of smoke and other undesirable gases resulting from the cauterising or other procedure, since the vacuum pump would extract the smoke and other undesirable gases more rapidly than they would be discharged through the discharge control valve 32 when in the open state.

Otherwise, the apparatus 60 and the insufflator 61 are similar to the apparatus 1 the insufflator 10, and their operation is likewise similar to that of the apparatus 1 and the insufflator 10.

Referring now to FIG. 4 there is illustrated apparatus also according to the invention, indicated generally by the reference numeral 70, for insufflating a cavity 2, in this embodiment of the invention the stomach of a human or animal subject during a laparoscopic procedure. In this case a cryogenic procedure for freezing cancerous cells, a tumour or other cancerous growth in the stomach 2 is being carried out during the laparoscopic procedure. For convenience only the cavity 2 of the stomach of the subject is illustrated. The apparatus 70 comprises and insufflator 72, and the apparatus 70 and the insufflator 72 are substantially similar to the apparatus 1 and the insufflator 10 described with reference to FIG. 1, and similar components are identified by the same reference numerals.

In this embodiment of the invention the insufflating fluid comprises compressed carbon dioxide which is derived from a pressure vessel 73 containing the compressed carbon dioxide in liquid form. In this case, the pressure vessel 73 is located externally of the housing 11 of the insufflator 72, and the compressed carbon dioxide is piped from the pressure vessel 73 to the pressure regulating valve 14 in the housing 11 of the insufflator 72. Otherwise the delivery and supply of the insufflating gas from the pressure regulating valve 14 through the flow control valve 16 through the supply conduit 17 to the first trocar 5 and to the cavity 2 is similar to that described with reference to the apparatus 1 of FIG. 1.

In this embodiment of the invention the discharge control means comprises an evacuating means, which in this case is provided by a vacuum pump 75 which is located in the housing 11 of the insufflator 72 and is similar to the vacuum pump 52 of the apparatus 50 described with reference to FIG. 2. An output conduit 76 from the outlet port 30 of the second trocar 6 connects the vacuum pump 75 to the second trocar 6 for drawing insufflating gas from the cavity 2.

In this embodiment of the invention the flow control valve 16 and the vacuum pump 75 are operated solely in response to the pressure in the cavity 2.

In this embodiment of the invention the cryogenic procedure is carried out by delivering liquid nitrogen through a suitable instrument (not shown) in the cavity 2 directly to the cancerous cells, tumour or other cancerous growths for freezing thereof. The instrument for delivering the liquid nitrogen to the cancerous cells, tumour or other cancerous growths will be well known to those skilled in the art, and terminates in a nozzle from which a jet of the liquid nitrogen is directed directly and precisely to the cells, tumour or growths to be freezed. The liquid nitrogen delivery instrument typically is introduced through the central bore in one of the first and second trocars 5 and 6. On exiting the nozzle of the delivery instrument the liquid nitrogen rapidly converts to gas, and rapidly expands, thus rapidly increasing the pressure within the cavity 2.

A selectable predefined working pressure in the range of 5 mm mercury to 20 mm mercury is inputted to the microcontroller 18 through the keypad 44. In this embodiment of the invention the selectable predefined working pressure entered into the microcontroller 18 through the keypad 44 is approximately 15 mm mercury. A selectable predefined maximum pressure is also entered into the microcontroller 18 through the keypad 44 which may lie in the range of 15 mm mercury to 30 mm mercury, and in this case, is approximately 20 mm mercury. A selectable predefined minimum pressure is also entered through the keypad 44 into the microcontroller 18 and may lie in the range of 5 mm mercury to 15 mm mercury and in this embodiment of the invention is approximately 10 mm mercury.

In this embodiment of the invention, the microcontroller 18 is programmed to operate the flow control valve 16 and the vacuum pump 75 as follows. During normal operation of the apparatus 70 and the insufflator 72 the vacuum pump 75 is deactivated. The microcontroller 18 operates the flow control valve 16 to deliver insufflating gas to the cavity 2 through the supply conduit 17 and in turn through the first trocar 5. The microcontroller 18 in response to signals read from the pressure sensor 40 controls the operation of the flow control valve 16 for maintaining the pressure of the insufflating gas in the cavity 2 substantially constant at the predefined working pressure.

In the event of the signals read from the pressure sensor 40 by the microcontroller 18 being indicative of the pressure of the insufflating gas in the cavity 2 exceeding the predefined maximum pressure, which would typically result from expansion of the liquid nitrogen within the cavity 2, the microcontroller 18 activates the vacuum pump 75 for in turn drawing insufflating gas and nitrogen from the cavity 2, and simultaneously, the microcontroller 18 operates the flow control valve 16 for shutting off the supply of insufflating gas to the cavity 2. The microcontroller 18 also activates the piezoelectric sounder 45 to output a first audible alarm signal indicating that the pressure in the cavity 2 has exceeded the predefined maximum pressure.

The microcontroller 18 maintains the vacuum pump 75 active and the flow control valve 16 shut off until signals read from the pressure sensor 40 are indicative of the pressure in the cavity 2 having reduced to or just below the predefined working pressure. At this stage the microcontroller 18 deactivates the vacuum pump 75, and again operates the flow control valve 16 for maintaining the pressure of the insufflating gas in the cavity 2 at the predefined working pressure.

In the event of the signals read from the pressure sensor 40 by the microcontroller 18 being indicative of the pressure in the cavity 2 falling to or just below the predefined minimum pressure, the microcontroller 18 if the vacuum pump 75 is activated, deactivates the vacuum pump 75 and operates the flow control valve 16 to increase the flow rate of insufflating gas to the cavity 2 until the pressure in the cavity 2 is returned to the predefined working pressure. At that stage the microcontroller 18 continues to operate the flow control valve 16 for maintaining the pressure in the cavity 2 at predefined working pressure. The microcontroller 18 also operates the piezoelectric sounder 45 to produce an audible alarm signal in the event of the pressure of the insufflating gas in the cavity 2 falling to or just below the predefined minimum pressure.

In the event of the pressure in the cavity 2 remaining above the predefined maximum pressure for more than a continuous predefined time period, which in this embodiment of the invention is approximately five seconds, the microcontroller 18 again operates the piezoelectric sounder 45 to produce a second audible alarm signal indicating that the pressure in the cavity 2 has remained above the predefined maximum pressure continuously for more than five seconds. On receiving the second audible alarm signal, the surgeon may decide to pause the cryogenic procedure, in order to allow the pressure within the cavity 2 to fall below the predefined maximum working pressure.

It is also envisaged that the operation of the vacuum pump 75 and the flow control valve 16 could be operated by the microcontroller 18 in response to externally first and second control signals, which, for example, could be produced by a foot pedal operated electric switch, similar to the foot pedal operated switch 35 of the embodiments of the apparatus 1 and 50 of FIGS. 1 and 2. In which case, a surgeon simultaneously with or just before or just after commencing the cryogenic procedure would depress the foot pedal 36 of the switch 35 in order to produce the first control signal, and would continuously operate the foot pedal 36 in the depressed state thereby maintaining the switch 35 in the closed circuit state until the cryogenic procedure had been completed, at which stage the surgeon would remove his foot from the foot pedal 36 thereby operating the switch 35 from the closed circuit state to the normally open circuit state to produce the second control signal.

On the microcontroller 18 detecting the first control signal as the switch 35 is operated from the normally open circuit state to the closed circuit state, the microcontroller 18 would output a first signal to the vacuum pump 75 to activate the vacuum pump 75 in order to extract the nitrogen gas from the cavity 2, and would operate the flow control valve 16 to shut off the supply of insufflating gas to the cavity 2. The microcontroller 18 would maintain the vacuum pump 75 in the active state and the flow control valve 16 in the shut off state until the second control signal from the foot pedal operated electric switch 35 is received, and at which stage the microcontroller 18 would output the second signal to the vacuum pump 75 to deactivate the vacuum pump 75, and would operate the flow control valve 16 in response to signals read from the pressure sensor 40 for maintaining the pressure in the cavity 2 at the predefined working pressure.

Referring now to FIGS. 5 and 6 there is illustrated apparatus according to another embodiment of the invention, indicated generally by the reference numeral 80 for insufflating a cavity 2 in the body of a human or animal subject, in this case the stomach 2 of a human or animal subject during a cryogenic procedure. The apparatus 80 comprises an insufflator 81, and both the apparatus 80 and the insufflator 81 are substantially similar to the apparatus 70 and the insufflator 72, and similar components are identified by the same reference numerals.

The main difference between the apparatus 80 and the apparatus 70 is that the apparatus 80 is suitable for carrying out a cryogenic procedure in the stomach 2 with an endoscope 82, rather than through a pair of trocars. The endoscope 82 is suitable for accessing the stomach 2 orally through the oesophagus 83. In this embodiment of the invention the input conduit 17 for supplying the insufflating gas to the stomach 2 and the output conduit 76 are connected to a single communicating conduit 84 by a three-way connector, namely, a Y-connector 85 externally of the subject, and the communicating conduit 84 is configured for passing into the stomach 2 of the subject through the oesophagus 83 either nasally or orally alongside the endoscope 82 but externally of the endoscope 82. The pressure sensor 40 is located in a recess 90 in an outer surface 86 of the communicating conduit 84 adjacent a distal end 87 thereof. An electrically conductive cable 88 extends from the pressure sensor 40 along the communicating conduit 84 and is secured thereto, and connects the pressure sensor 40 to the microcontroller 18.

A liquid nitrogen delivery instrument and other instruments are passed into the stomach 2 of the subject through the endoscope 82 as will be understood by those skilled in the art. A suitable seal (not shown) is located adjacent an upstream end 89 of the endoscope 82 for sealing against catheters, conduits, tubes and other instruments which are passed through the endoscope 82 into the stomach 2 in order to minimise leakage of insufflating gas through the endoscope 82.

In use, the communicating conduit 84 is initially passed orally or nasally through the oesophagus 83 into the stomach 2 of the subject with the distal end 87 thereof and the pressure sensor 40 located in the stomach 2. The endoscope 82 is then passed orally into the stomach 2 through the oesophagus 83. The microcontroller 18 operates the flow control valve 16 into the open state for delivering and controlling the delivery of the insufflating gas into the stomach 2. The microcontroller 18 reads the signals from the pressure sensor 40 and controls the flow control valve 16 for controlling delivering of the insufflating gas to the stomach 2 in order to maintain the pressure in the stomach 2 at the predefined working pressure, which in this embodiment of the invention is a pressure of 15 mm mercury.

On the microcontroller 18 determining from the signals read from the pressure sensor 40 that the signals are indicative of the pressure in the stomach 2 exceeding the predefined maximum pressure, which in this embodiment of the invention is 20 mm mercury, for example, as a result of the expansion of liquid nitrogen in the stomach 2 to gas, the microcontroller 18 immediately activates the vacuum pump 75 to evacuate the stomach 2, and operates the flow control valve 16 into the closed state thereby shutting off delivery of the insufflating gas to the stomach 2. The microcontroller 18 also operates piezoelectric sounder 45 to produce the first audible alarm signal. The microcontroller 18 maintains the vacuum pump 75 in the active state and maintains the flow control valve 16 in the closed state until the signals read from the pressure sensor 40 are indicative of the pressure in the stomach 2 having fallen to or just below the predefined working pressure. At that stage the microcontroller 18 deactivates the vacuum pump 75 and operates the flow control valve 16 to commence delivery of the insufflating gas into the stomach 71.

In the event of the pressure in the cavity 2 remaining above the predefined maximum pressure continuously for the predefined time period, which in this embodiment of the invention is also five seconds, the microcontroller 18 operates the piezoelectric sounder 45 to produce the second audible alarm signal indicating that the pressure in the cavity 2 has remained above the predefined maximum pressure continuously for the period of five seconds.

In the event of the signal read from the pressure sensor 40 being indicative of the pressure in the stomach 2 falling to or just below the predefined minimum pressure the apparatus 80 and the insufflator 81 operate in a similar manner to that described in connection with the apparatus 70 and the insufflator 72 described with reference to FIG. 4.

Otherwise the apparatus 80 and the insufflator 81 and their use and operation is similar to that of the apparatus 70 and the insufflator 72 described with reference to FIG. 4.

Referring now to FIG. 7 there is illustrated apparatus according to another embodiment of the invention indicated generally by the reference numeral 95 for insufflating a cavity 2 in the body of a human or animal subject during a procedure, for example, a laparoscopic procedure. The apparatus 95 comprises an insufflator 96, and both the apparatus 95 and the insufflator 96 are substantially similar to the apparatus 1 and the insufflator 10 of FIG. 1, and similar components are identified by the same reference numerals. The main difference between the apparatus 95 and the insufflator 96 of FIG. 7 and the apparatus 1 and the insufflator 10 of FIG. 1 is that instead of the pressure sensor 40 being located on one of the trocars, in this embodiment of the invention the pressure sensor 40 is located at the proximal end 97 of a Veress needle 98, which is inserted through the abdominal wall 8 of the subject. A distal pointed end 97 of the Veress needle 98 is located in the cavity 2. In this case, the cable 42 from the pressure sensor 40 is also connected to the microcontroller 18 so that the microcontroller 18 can monitor the pressure of the insufflating air in the cavity 2. In this embodiment of the invention the air column in the bore of the Veress needle 98 is static, so that the pressure detected by the pressure sensor 40 is the static pressure of the insufflating air in the cavity 2.

Otherwise, the apparatus 95 and the insufflator 96 is similar to the apparatus 1 and the insufflator 10 of FIG. 1 and its operation is likewise similar.

It will also be appreciated that in the other embodiments of the invention described with reference to FIGS. 2 to 6, instead of locating the pressure sensor 40 on one of the trocars, or the communicating conduit 84, as the case may be, the pressure sensor may be located on a Veress needle similar to the Veress needle 98, the distal end of which would be inserted into the cavity being insufflated.

It is also envisaged that instead of the pressure sensor 40 being located on the proximal end of the Veress needle, the pressure sensor could be located adjacent the point distal tip of the Veress needle, and the cable 42 from the pressure sensor 40 would extend through the bore of the Veress needle and in turn to the microcontroller 18.

It is also envisaged that the insufflating air or gas, as the case may be, may be delivered to the cavity through the Veress needle instead of through one of the trocars.

It will of course be appreciated that while some of the apparatus have been described as comprising a discharge control valve, the discharge control valve could be replaced by a vacuum pump, similar to the vacuum pump 52 of the apparatus 50, and in which case, the period during which the vacuum pump 52 would be activated would be similar to the period during which the discharge control valve would operate in the second open state timed by the timer 65. Similarly, it will be appreciated that those apparatus in which the discharge control means is provided by a vacuum pump, the vacuum pump could be replaced with a discharge control valve, or other discharge control means.

While the pressure sensors 40 have been described as being located on the distal end of the first trocar 5 in the embodiments of FIGS. 1 to 4, and on the distal end of the communicating conduit 84 of the embodiment of FIGS. 5 and 6, the pressure sensor could be located on any suitable part of the first trocar 5, the communicating conduit or indeed on the endoscope 82. Indeed, in certain cases, it is envisaged that the pressure sensor 40 may be provided on a pressure sensor carrier which would be inserted through the bore 21 of the one of the trocars or a bore through the endoscope 82 into the cavity. Alternatively, it is envisaged that the pressure sensor 40 may be located on the second trocar 6.

It is also envisaged that instead of the pressure sensor 40 being located in the cavity, the pressure sensor may be located in the housing 11, or otherwise externally of the cavity and in which case, the pressure sensor would monitor the pressure in a conduit extending from the cavity, which could extend into the cavity through the bore of one of the trocars or through a bore in the endoscope 82, and the insufflating air or gas in the conduit would be static so that the pressure read by the pressure sensor would be the static pressure in the cavity.

While the insufflating fluid has been described as comprising insufflating air or carbon dioxide, any other suitable insufflating fluid may be used. For example, it is envisaged in certain cases that the insufflating fluid may be any suitable gas, for example any suitable inert gas.

Additionally, it will be appreciated that when the insufflating fluid is provided as air, the air supply may be provided by an air blower or any other suitable means for providing a supply of insufflating air at a suitable pressure.

It will be appreciated that while electrical signals between the microcontroller, the pressure sensor and between the microcontroller and the discharge control means, and between the microcontroller and the switch 35 of the foot pedal operated switch and between the microcontroller and the status monitoring means have been described as being transmitted through cables and/or wires, it is envisaged that in many cases communications between the microcontroller and some or all of the various pressure sensor, status monitoring sensor, valves, switches and vacuum pumps the like may be carried out wirelessly, for example, by Bluetooth or by other such wireless communicating means.

While the discharge control valve has been described as comprising a bi-state valve which in the first state is in the closed state, and in the second state is in the fully open state, it is envisaged that in certain cases, the discharge control valve may be configured so that in the first state, instead of being fully closed, the discharge control valve would be in a state which would permit limited leakage of insufflating air or gas therethrough in order to provide controlled leakage of the insufflating air or gas from the cavity.

It is also envisaged that the discharge control valve, instead of being a bi-state valve, may be a multi-state valve, which would be operable between a first state and a second state through a plurality of intermediate states, and indeed, could be operable between the first and second state through an infinite number of intermediate states. In which case, an analogue control system would be provided to control the discharge control valve so that the rate of discharge of the insufflating air through the discharge control valve could be varied, and most likely would be infinitely variable, in order to allow the flow rate of the insufflating fluid through the cavity to be varied depending on the volume of smoke or other undesirable gases to be removed from the cavity, and the speed with which the smoke and other undesirable gases are to be removed from the cavity, and similarly depending on the speed with which it is necessary that the gases resulting from the cryogenic procedure be removed, and also depending on the pressure of the insufflating fluid in the cavity. For example, as the pressure of the insufflating fluid in the cavity commences to drop towards the predefined working pressure, it may be desired to reduce the rate at which the insufflating fluid is being discharged through the discharge control valve regressively.

It is also envisaged that instead of locating the pressure monitoring means within the cavity, the pressure monitoring means may be located externally of the cavity, for example, in the housing 11, and the pressure monitoring means would monitor the air pressure in the conduit 17, for example, at a location where the conduit 17 is connected to the flow control valve. In which case, the resistance to flow of the insufflating air through the conduit 17 and in turn through the inlet port 23 and the first trocar 5 to the cavity would be determined, as well as the pressure drop which would result from this flow resistance. A correction factor which would be a function of the pressure drop would then be computed, and the microcontroller would be programmed to apply the correction factor to the pressure read from the pressure monitoring means in order to determine the exact pressure in the cavity. It is also envisaged that when determining the correction factor, a number of correction factors could be computed which would take account of the type and size of the cables, tubes, catheters and the like being passed through the bore of the trocar 5, since the resistance to flow of the insufflating air would vary, depending on the size of such tubes, catheters, cables and the like in cases where the insufflating air is delivered directly from the inlet port through the bore 21 extending through the first trocar 5. These correction factors would then be stored in the microcontroller, and a surgeon could input through the keypad the appropriate correction factor to be applied to the pressure read from the pressure monitoring means in the conduit 17 adjacent the flow control valve 16 in order to determine the correct pressure of the insufflating air in the cavity.

It will also be appreciated that while the flow control valve and the discharge control valve have been described as being electrically operated, the various valves could be pneumatically operated or could be operated by any other suitable means.

In cases where the discharge control valve is provided as an analogue type valve, the discharge control valve would be operated by a motor, which may be an electrically powered or pneumatically powered motor.

It will also be appreciated that in the embodiment of the invention described with reference to FIG. 3, instead of the signal indicating operation of the cauterising or other such instrument being derived from a status monitoring means which would be mounted on the instrument, the signal indicative of the operation of the cauterising instrument or other such relevant instrument and/or the commencement and/or termination of operation of the cauterising instrument or other such relevant instrument may be derived from a control system which would control the operation of the cauterising instrument or other such instrument under the control of the surgeon. In which case, the signal indicative of the commencement of operation of the cauterising instrument or other relevant instrument could be derived from the signal from the control system which causes the cauterising instrument or other such instrument to commence operation, and the signal indicative of termination of operation of the cauterising instrument or other such relevant instrument would be derived from the signal from the control system terminating operation of the cauterising instrument or other relevant instrument.

Additionally, it is envisaged that in cases where the cauterising instrument or other such relevant instrument or cryogenic instrument is operated by a foot pedal operated electric switch, the externally generated first and second control signals may be derived from the foot pedal operated switch. In which case, the first control signal would be derived from depression of the foot pedal in order to operate the foot pedal operated switch to activate the cauterising instrument, and the second control signal would be derived from the foot pedal operated switch being operated to terminate the cauterising, cryogenic or other procedure. In which case, on receiving the first control switch from the foot pedal controlled switch which operated the cauterising or other instrument, the microcontroller 18 would output the first signal to the discharge control valve or to the vacuum pump, as the case may be, to operate the discharge control valve from the first state to the second state or to activate the vacuum pump, and on receiving the second control signal from the foot pedal operated switch to deactivate the cauterising or other instrument, the microcontroller 18 would output the second signal to the discharge control valve or to the vacuum pump, as the case may be, to operate the discharge control valve from the second state to the first state, or to deactivate the vacuum pump, as the case may be.

Similarly, in the case of the apparatus and insufflators of FIGS. 4 to 6, the externally generated first and second control signals for applying to the microcontroller 18 for operating the discharge control valve, or the vacuum pump as the case may be, may be derived from signals which open and close valves for delivering the nitrogen to the delivery instrument which delivers the nitrogen to the cancerous cells, tumours or growth to be freezed, and in which case, on receiving the first control signal indicative of the valve supplying the nitrogen to the delivery instrument being operated into the open state, the microcontroller would operate the discharge control valve from the first state to the second state, or would activate the vacuum pump, as the case may be, and on receiving the second control signal indicative of the valve supplying the nitrogen to the delivery instrument being operated into the closed state, the microcontroller 18 would operate the discharge control valve from the second state to the first state or deactivate the vacuum pump, as the case may be.

It is also envisaged that the apparatus and insufflator of FIGS. 1 to 3 could also be used for insufflating a cavity in conjunction with a cryogenic procedure being carried out in the cavity. In which case, it is envisaged that a signal indicative of commencement of the operation of the cryogenic instrument for delivering the liquid nitrogen would be used for activating either the discharge control valve of the embodiments of the insufflators of FIGS. 1 to 3 or the vacuum pump of the insufflator of FIG. 2 to commence discharging or drawing insufflating air or gas from the cavity.

The microcontroller in response to signals read from the pressure sensor would operate the flow control valve to increase the flow rate of insufflating air or gas to the cavity, thereby increasing the flow of insufflating gas through the cavity for removing the expanding nitrogen gas. Alternatively, a surgeon carrying out the cryogenic procedure could operate the foot pedal operated switch of the insufflators of FIGS. 1 and 2 on commencement of the cryogenic procedure, and would operate the foot pedal operated switch in the closed state until the expanded nitrogen gas would be removed.

While the electronic control means has been described as comprising a microcontroller, any other suitable electronic control means may be provided, for example, a signal processing means, a signal processor, a microprocessor, a programmable logic controller, or any other suitable control means.

While the discharge control means, in the embodiment of the invention of FIGS. 4 to 6 has been described as comprising an evacuating means, namely, a vacuum pump, other suitable evacuating means may be provided, and in certain cases, it is envisaged that an exhaust valve may be sufficient for evacuating the stomach or other cavity in the event of the pressure therein exceeding the predefined maximum pressure. In the event of the evacuating means being provided by an exhaust valve, it is envisaged that the exhaust valve could be operated in a fully open state for evacuating the stomach or other cavity, and in a fully closed state, as well as in one or more intermediate states for providing controlled leakage from the stomach, for example, in the event of it being desired to evacuate other gases, for example, smoke and other gases resulting from cauterising and the like. It will also, of course, be appreciated that where the evacuating means is provided by a vacuum pump, the vacuum pump could also be operated for removing undesirable gases from the stomach or other cavity of the human or animal subject, such as, for example, smoke and other gases resulting from cauterising.

Indeed, it is also envisaged that the discharge control means may comprise both a vacuum pump and an exhaust valve. It is envisaged that where the evacuating means is provided by an exhaust valve, the exhaust valve would be located adjacent the outlet port from the outlet trocar, and in general, would be directly coupled to the outlet port. Alternatively, in the case of the apparatus 80 the exhaust valve could be located on the port of the Y-connector to which the output conduit is connected, but in this case the output conduit would be disconnected from the Y-connector and replaced by the exhaust valve.

It is also envisaged that an automatic pressure release valve may be connected to the common communicating conduit 84 adjacent the Y-connector 85, or connected to the outlet conduit, preferably adjacent the Y-connector 85 which would be set to automatically transition from a closed state to an open state in the event of the pressure in the common communicating conduit 84 or the outlet conduit exceeding a predefined safe working pressure, which typically, could be a pressure with the range of 20 mmHg to 30 mmHg.

It will also be appreciated that other suitable cryogenic liquids or gases may be used for freezing the cells or tumour.

While the apparatus of FIGS. 4 to 6 have been described for carrying out a cryogenic procedure in the stomach of a subject, it will be readily apparent to those skilled in the art that the apparatus may be used for carrying out a cryogenic procedure in any other cavity lumen, vessel or organ of a subject, for example, the apparatus may be used for carrying out a cryogenic treatment in the oesophagus, the lungs, in the perineum cavity, uterus or in any other vessel, lumen or organ.

While specific values for the predefined working pressure and the predefined maximum pressure and the predefined minimum pressure have been described, it will be readily apparent to those skilled in the art that the predefined working pressure, the predefined maximum pressure and the predefined minimum pressure will be dependent upon the lumen, vessel or organ in which the procedure is being carried out and also on the procedure being carried out.

It will also be appreciated that a predefined time may elapse during which the pressure in the cavity vessel, lumen or organ may exceed the predefined maximum pressure or fall below the predefined minimum pressure before an alarm signal is sounded and such a predefined time period would be dependent upon the lumen, vessel cavity or organ in which the procedure is being carried out, and on the procedure being carried out.

While the alerting means has been described as comprising a piezoelectric sounder, any other suitable alarm generating means may be provided, and in certain cases, it is envisaged that the alarm generating means as well as or instead of producing an audible alarm signal may produce a visual alarm signal, or could produce both an audible and a visual alarm signal.

It will also be appreciated that while the flow control means has been described as comprising a motorised flow control valve, any other suitable flow control valve may be used, for example, in certain cases, it is envisaged that the flow control valve may be a solenoid operated valve.

While the apparatus of FIGS. 1 to 4 and 7 has been described as comprising a pair of trocars, in certain cases, it is envisaged that a single trocar may be sufficient. Additionally, in cases where a single trocar is provided, it will be appreciated that the outlet port and the inlet port will be provided on the same trocar. Indeed, it is envisaged that where the apparatus is provided with two trocars, namely, one inlet trocar and one outlet trocar, it is envisaged that both the inlet port and the outlet port could be provided on one of the trocars, and the other trocar could be provided, for example, for introducing the liquid nitrogen delivery instrument as well as other instruments to the stomach.

It is also envisaged that where the apparatus is being used with one or more trocars, it is envisaged that the inlet and outlet conduits of the apparatus of FIGS. 1 to 4 and 7 could also be connected by a Y-connector or other suitable connecting means to a single communicating conduit, such as the communicating conduit 84 of the apparatus of FIGS. 5 and 6, and the single communicating conduit would be passed into the cavity in which the procedure is being carried out through one of the trocars.

It is also envisaged that instead of the communicating conduit being passed into the stomach or other cavity through the oesophagus but externally of the endoscope of the apparatus of FIGS. 4 and 6, the communicating conduit could be passed into the stomach or other cavity through the endoscope. Further, it is envisaged that an upstream port may be located in the wall of the endoscope adjacent the upstream end of the endoscope, and a corresponding lumen would extend through the wall of the endoscope from the upstream port, and would terminate in a corresponding downstream port adjacent the downstream end of the endoscope, and the communicating conduit 53 could be connected to the upstream port for communicating the communicating conduit with the stomach or other cavity.

It will of course be appreciated that while the endoscope of the apparatus of FIGS. 5 and 6 has been described and illustrated for carrying out a cryogenic procedure in the stomach, the endoscope and the apparatus could also be used for carrying out a cryogenic procedure in the oesophagus and the small intestines where the endoscope and the communicating conduit would be introduced orally into the subject. It will also be appreciated that the endoscope and the apparatus of FIGS. 5 and 6 may be adapted for carrying out a cryogenic procedure or any other procedure in the rectum, the bowel and the large intestine or in the small intestine adjacent the large intestine, where the endoscope and the communicating conduit would be passed rectally into the subject.

While the evacuating means has been described as comprising the vacuum pump, it is also envisaged that any other suitable means for drawing a vacuum may be used, and in certain cases, it is envisaged that a venturi system could be used for drawing the vacuum. Needless to say, any other suitable vacuum drawing means could be provided.

The invention claimed is:

1. A method for removing an undesirable gas from a cavity in the body of a human or animal subject during insufflating of the cavity, the undesirable gas resulting from a procedure being carried out with an instrument in the cavity, the method comprising:

delivering insufflating fluid to the cavity through a flow control valve, monitoring a pressure of the insufflating fluid in the cavity, operating the flow control valve to maintain the pressure of the insufflating fluid in the cavity at a predefined working pressure in response to the monitored pressure of the insufflating fluid in the cavity, providing a discharge control means for controlling discharge of insufflating fluid from the cavity, the discharge control means being selectively and alternately operable in a first state to prevent discharge of the insufflating fluid from the cavity, and in a second state for permitting flow of the insufflating fluid from the cavity to remove the undesirable gas therefrom, the discharge control means being operable from the first state to the second state in response to one of a first electrical control signal and a first pneumatic control signal, and being operable from the second state to the first state in response to one of a second electrical control signal and a second pneumatic control signal, the first electrical control signal comprising one of
an electrical signal generated by a manually operated electrical switch in a first state thereof, and
an electrical signal indicative of operation of or commencement of operation of the instrument in the cavity generated by one of a status sensor monitoring operational status of the instrument, and an instrument control system controlling operation of the instrument, the second electrical control signal comprising one of
an electrical signal generated by the manually operated electrical switch in a second state thereof,
an electrical signal indicative of ceasing of operation of the instrument in the cavity generated by one of the status sensor monitoring operational status of the instrument, and the instrument control system controlling operation of the instrument, and
an electrical signal generated by a timer, timing out a predefined time period from commencement of operation of the instrument in the cavity or from ceasing of operation of the instrument in the cavity, the method further comprising:
operating the discharge control means from the first state to the second state to increase a rate at which the insufflating fluid is discharged from the cavity in response to the first electrical control signal or the first pneumatic control signal, operating the discharge control means from the second state to the first state in response to the second electrical control signal or the second pneumatic control signal, the discharge control means being maintained in the second state between an occurrence of the first electrical control signal or the first pneumatic control signal and an occurrence of the second electrical control signal or the second pneumatic control signal, and operating the flow control valve in response solely to the monitored pressure in the cavity for maintaining the pressure of the insufflating fluid in the cavity at the predefined working pressure while the discharge control means is operating in the second state to temporarily increase the flow of insufflating fluid to the cavity, for in turn temporarily increasing the flow rate of the insufflating fluid through the cavity for removing the undesirable gas.

2. The method as claimed in claim 1 in which the flow rate of the insufflating fluid is increased in response to the pressure in the cavity falling below the predefined working pressure.

3. The method as claimed in claim 1 further comprising providing a pressure sensor for monitoring the pressure of the insufflating fluid indicative of the pressure of the insufflating fluid in the cavity.

4. The method as claimed in claim 3 in which the pressure sensor is located in the cavity.

5. The method as claimed in claim 1 in which the predefined time period is timed from the ceasing of operation of the instrument in the cavity.

6. The method as claimed in claim 1 in which the manually operated electrical switch comprises an electrical bistate switch.

7. The method as claimed in claim 6 in which the electrical bistate switch comprises one of a hand operated electrical bistate switch and a foot pedal operated electrical bistate switch.

8. The method as claimed in claim 1 in which the discharge control means comprises one of a discharge control valve and a vacuum pump.

9. The method as claimed in claim 1 in which the predefined working pressure is selectable, and lies in the range of 5 mmHg to 15 mmHg.

10. The method as claimed in claim 1 in which the flow control valve is operated in response to the monitored pressure of the insufflating fluid in the cavity under the control of a signal processor, and the discharge control means is operated in response to the first and second electrical control signals or the first and second pneumatic control signals under the control of the signal processor.

11. The method as claimed in claim 1 in which the discharge control means is operated from the second state to the first state in response to the pressure in the cavity falling below a predefined minimum pressure.

12. The method as claimed in claim 11 in which the predefined minimum pressure is selectable, and lies in the range of 5 mmHg to 10 mmHg.

13. The method as claimed in claim 1 in which a filter is located downstream of the discharge control means.

14. The method as claimed in claim 1 in which the flow control valve comprises a variable state flow control valve.

15. The method as claimed in claim 1 in which the insufflating fluid comprises one of compressed air, compressed carbon dioxide and a compressed inert gas.

16. The method as claimed in claim 1 in which the instrument comprises an instrument, the operation of which results in the generation of smoke or an undesirable gas in the cavity.

17. The method as claimed in claim 1 in which the discharge control means is operable from the first state to the second state in response to the pressure in the cavity exceeding a predefined maximum pressure.

18. The method as claimed in claim 17 in which the predefined maximum pressure is selectable, and lies in the range of 15 mmHg to 30 mmHg.

19. A method for removing an undesirable gas from a cavity in the body of a human or animal subject during insufflating of the cavity, the undesirable gas resulting from a procedure being carried out with an instrument in the cavity, the method comprising:
    delivering insufflating fluid to the cavity through a flow control valve,
    monitoring a pressure of the insufflating fluid in the cavity,
    operating the flow control valve to maintain the pressure of the insufflating fluid in the cavity at a predefined working pressure in response to the monitored pressure of the insufflating fluid in the cavity,
    providing a discharge control means for controlling discharge of insufflating fluid from the cavity, the discharge control means being selectively and alternately operable in a first state to prevent discharge of the insufflating fluid from the cavity, and in a second state for permitting flow of the insufflating fluid from the cavity to remove the undesirable gas therefrom, the discharge control means being operable from the first state to the second state in response to one of a first electrical control signal and a first pneumatic control signal, and being operable from the second state to the first state in response to one of a second electrical control signal and a second pneumatic control signal,
    the first electrical control signal comprising one of
        an electrical signal generated by a manually operated electrical switch in a first state thereof, and
        an electrical signal indicative of operation of or commencement of operation of the instrument in the cavity generated by one of a status sensor monitoring operational status of the instrument, and an instrument control system controlling operation of the instrument,
    the second electrical control signal comprising one of
        an electrical signal generated by the manually operated electrical switch in a second state thereof,
        an electrical signal indicative of ceasing of operation of the instrument in the cavity generated by one of the status sensor monitoring operational status of the instrument, and the instrument control system controlling operation of the instrument, and
        an electrical signal generated by a timer, timing out a predefined time period from the commencement of operation of the instrument in the cavity or from ceasing of operation of the instrument in the cavity,
    the method further comprising:
    operating the discharge control means from the first state to the second state to increase a rate at which the insufflating fluid is discharged from the cavity in response to the first electrical control signal or the first pneumatic control signal,
    operating the discharge control means from the second state to the first state in response to the second electrical control signal or the second pneumatic control signal,
    the discharge control means being maintained in the second state between an occurrence of the first electrical control signal or the first pneumatic control signal and an occurrence of the second electrical control signal or the second pneumatic control signal, and
    operating the flow control valve in response to the monitored pressure in the cavity for maintaining the pressure of the insufflating fluid in the cavity at the predefined working pressure while the discharge control means is operating in the second state to temporarily increase the flow of insufflating fluid to the cavity, for in turn temporarily increasing the flow rate of the insufflating fluid through the cavity for removing the undesirable gas.

20. A method for removing an undesirable gas from a cavity in the body of a human or animal subject during insufflating of the cavity, the undesirable gas resulting from a procedure being carried out with an instrument in the cavity, the method comprising:
    delivering insufflating fluid to the cavity through a flow control means,
    monitoring a pressure of the insufflating fluid in the cavity,
    operating the flow control means to maintain the pressure of the insufflating fluid in the cavity at a predefined working pressure in response to the monitored pressure of the insufflating fluid in the cavity,
    providing a discharge control means for controlling discharge of insufflating fluid from the cavity,
    operating the discharge control means to increase the rate at which the insufflating fluid is discharged from the cavity in response to a first electrical control signal or a first pneumatic control signal,
    the first electrical control signal being derived from one of
        an electrical signal generated by a manually operated electrical switch in a first state thereof, and
        an electrical signal indicative of operation of or commencement of operation of the instrument in the cavity generated by one of a status sensor monitoring operational status of the instrument, and an instrument control system controlling operation of the instrument,
    operating the flow control valve in response solely to the monitored pressure in the cavity for maintaining the pressure of the insufflating fluid in the cavity at the predefined working pressure while the discharge control means is operating to increase a rate at which the insufflating fluid is being discharged from the cavity to temporarily increase the flow of insufflating fluid to the cavity, for in turn temporarily increasing the flow rate of the insufflating fluid through the cavity for removing the undesirable gas.

* * * * *